United States Patent
Ekin et al.

(10) Patent No.: US 11,602,396 B2
(45) Date of Patent: Mar. 14, 2023

(54) OSS FORESHORTENING DETECTION SYSTEMS, CONTROLLERS AND METHODS

(71) Applicant: KONINKLIJKE PHILIPS N.V., Eindhoven (NL)

(72) Inventors: Ahmet Ekin, Eindhoven (NL); Molly Lara Flexman, Melrose, MA (US); Paul Thienphrapa, Cambridge, MA (US); Willhelmus Henrica Gerarda Maria Van Den Boomen, Valkenswaard (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 343 days.

(21) Appl. No.: 16/496,571

(22) PCT Filed: Mar. 29, 2018

(86) PCT No.: PCT/EP2018/058103
§ 371 (c)(1),
(2) Date: Sep. 23, 2019

(87) PCT Pub. No.: WO2018/178248
PCT Pub. Date: Oct. 4, 2018

(65) Prior Publication Data
US 2021/0100622 A1  Apr. 8, 2021

Related U.S. Application Data

(60) Provisional application No. 62/478,818, filed on Mar. 30, 2017.

(51) Int. Cl.
*A61B 34/20* (2016.01)
*A61B 17/00* (2006.01)

(52) U.S. Cl.
CPC ........ *A61B 34/20* (2016.02); *A61B 17/00234* (2013.01); *A61B 2034/2061* (2016.02)

(58) Field of Classification Search
CPC .............. A61B 34/20; A61B 17/00234; A61B 2034/2061; A61B 17/00
See application file for complete search history.

(56) References Cited

U.S. PATENT DOCUMENTS

| 6,493,575 B1 | 12/2002 | Kesten |
| 2006/0064006 A1 | 3/2006 | Strommer |

(Continued)

FOREIGN PATENT DOCUMENTS

| EP | 2349004 | 8/2011 |
| WO | 201018488 | 2/2010 |

(Continued)

OTHER PUBLICATIONS

International Search Report and Written Opinion dated Jul. 9, 2018 for International Application No. PCT/EP2018/058103 Filed Mar. 29, 2018.

*Primary Examiner* — Joseph M Santos Rodriguez
*Assistant Examiner* — Kaitlyn E Sebastian

(57) ABSTRACT

An OSS foreshortening detection system employing an interventional device (40) including a OSS sensor (20) having shape nodes for generating shape sensing data informative of a shape of OSS sensor (20). The system further employs a OSS foreshortening detection device (80) including a OSS shape controller (90) for reconstructing a shape of a portion/entirety of interventional device (40) derived from a generation of the shape sensing data by OSS sensor (20). Device (80) further includes a OSS foreshortening controller (100) for monitoring any foreshortening of the interventional device (40) within an image of the interventional device (40) including the OSS foreshortening controller (100) detecting a location of any occurrence of a foreshort- (Continued)

ening of the interventional device (40) within the image of interventional device (40) derived from the reconstruction of the shape of the portion/entirety of interventional device (40) by the OSS shape controller (90).

17 Claims, 14 Drawing Sheets

(56) References Cited

U.S. PATENT DOCUMENTS

| | | | |
|---|---|---|---|
| 2008/0212082 A1* | 9/2008 | Froggatt | G01D 5/35316 356/73.1 |
| 2013/0216025 A1* | 8/2013 | Chan | A61B 6/488 378/63 |
| 2013/0303893 A1* | 11/2013 | Duindam | G16Z 99/00 600/424 |
| 2014/0371578 A1 | 12/2014 | Auvray | |
| 2015/0005865 A1 | 1/2015 | Bergman | |
| 2016/0073858 A1 | 3/2016 | Sato | |
| 2016/0327781 A1 | 11/2016 | Kuboi | |
| 2017/0039736 A1 | 2/2017 | Aben | |
| 2017/0281293 A1* | 10/2017 | Verstege | G06T 7/11 |
| 2018/0008352 A1* | 1/2018 | Flexman | A61B 34/20 |

FOREIGN PATENT DOCUMENTS

| | | |
|---|---|---|
| WO | 201041201 | 4/2010 |
| WO | 2010150145 | 12/2010 |

* cited by examiner

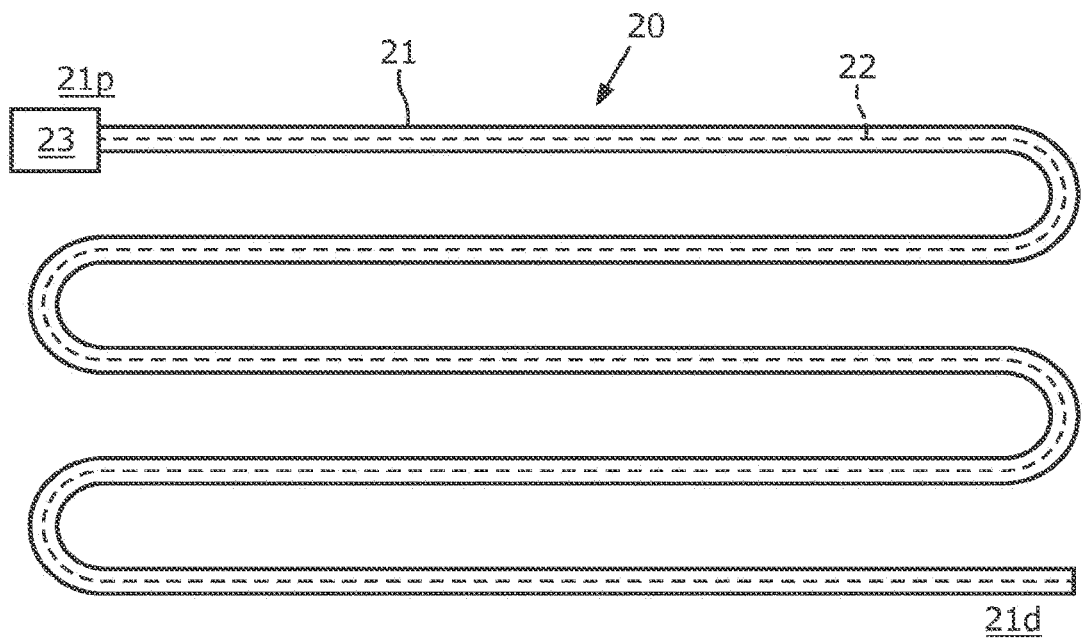
FIG. 2A
(Prior art)
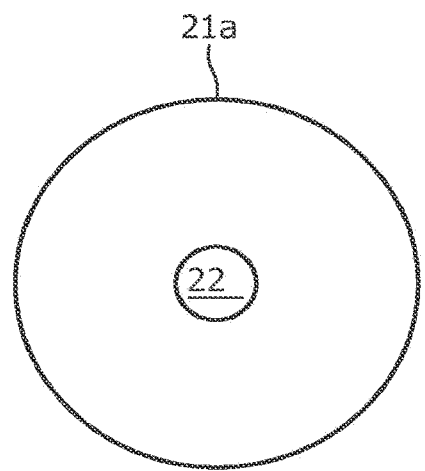 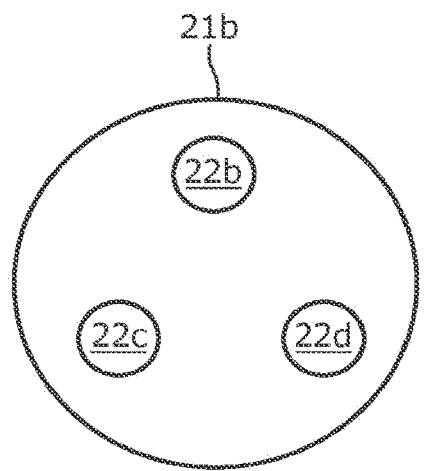
FIG. 2B            FIG. 2C
(Prior art)           (Prior art)

OSS FORESHORTENING DETECTION SYSTEMS, CONTROLLERS AND METHODS

CROSS REFERENCE TO RELATED APPLICATIONS

This application is the U.S. National Phase application under 35 U.S.C. § 371 of International Application No. PCT/EP2018/058103 filed Mar. 29, 2018, published as WO 2018/178248 on Oct. 4, 2018, which claims the benefit of U.S. Provisional Patent Application No. 62/478,818 filed Mar. 30, 2017. These applications are hereby incorporated by reference herein.

FIELD OF THE INVENTION

The inventions of the present disclosure generally relate to systems, controllers and methods for monitoring a potential of foreshortening of an interventional tool within an image of the interventional device.

The inventions of the present disclosure more particularly relate to improving such systems, controllers and methods by implementing optical shape sensing (OSS) technology to detect a location of any occurrence of foreshortening of an interventional device within an image of the interventional device.

BACKGROUND OF THE INVENTION

Optical shape sensing (OSS) uses light along a single core or a multicore optical fiber for device localization and navigation during surgical intervention. The principle involved makes use of distributed strain measurements in the optical fiber using characteristic Rayleigh backscatter or controlled grating patterns. The shape along the optical fiber begins at a specific point along the sensor, known as the launch or z=0, and the subsequent shape position and orientation of the optical fiber are relative to that point.

An OSS fiber may be integrated into an interventional tool (e.g., vascular tools, endoluminal tools and orthopedic tools) to thereby provide live visual guiding via a monitor of the interventional tool during a minimally invasive procedure whereby the integrated OSS fiber provides a position (i.e., a location and/or an orientation) of a portion or an entirety of the interventional tool. While the live visual guiding of the interventional tool has proven advantageous for facilitating a successful minimally invasive procedure, issues of "pushability" and "torquability" of the interventional tool are a concern to potential "buckling" and a potential "whipping" of the interventional tool.

A key feature of shape sensing of an optical fiber is that it provides three-dimensional ("3D") information about the entire shape of a device having the optical fiber embedded therein. A challenge is, then, how to properly visualize and communicate the 3D information to a device operator of an image of the device, particularly when the device is being registered to an imaging modality or navigated within an anatomical region. Currently, visualization and communication of the 3D information may be accomplished by showing two (2) two-dimensional ("2D") projections of the device shape in side-by-side 90° offset projections (e.g., side-by-side display of AP and Lateral projections). Other techniques could include 3D displays, augmented reality glasses, etc. Regardless, a key challenge remains in helping the device operator interpret the 3D information contained in the displayed device shape.

One common issue in complex manipulation of devices in 2D x-ray imaging (or fluoroscopy) is foreshortening. This occurs when the device takes a path with an angle towards the device operator (or, in the case of x-ray, a path that is in line with the source and detector). For example, FIG. 1A shows an actual 3D shape and 3D length of a device 10 as captured in a 2D lateral projection image 11. To the contrary, FIG. 1B shows the same device 10 in a 2D AP projection image 12 whereby the 3D shape of device 10 in accurately appears to be straight and the 3D length of device 10 appears to be shorter than the actual 3D length of device 10.

Foreshortening is especially important when deploying therapy, such as a balloon, stent, or endograft. In most cases, the therapy delivered must cover the appropriate region in order to be effective. If foreshortening is identified, it can be addressed by changing the perspective of the image. For example, if foreshortening of device 10 is identified in 2D AP projection image 12 (FIG. 1), then the imaging modality may be repositioned from an AP position associated with th 2D AP projection image 12 to a lateral position for generating the lateral projection image 11 (FIG. 1A) (e.g., a c-arm of an x-ray modality may be rotated from an AP position to a lateral position). However, often it is not obvious to the device operator that foreshortening of device is occurring in a particular image.

Foreshortening is also relevant during registration. For example, during an OSS registration (e.g., unicath length or position of a therapy device), the device operator clicks on the relevant point in an x-ray image of the device embedding the OSS optical fiber and the nearest point on the OSS shape is used for registration purposes. If there is no foreshortening, this can be done on a single x-ray projection. However, if there is foreshortening then the nearest point is uncertain and this can lead to errors in registration.

While systems and methods have been developed to monitor foreshortening, there still exists a need for visualizing foreshortening of 3D OSS shapes and identifying when foreshortening could impact registration or other similar algorithms.

SUMMARY OF THE INVENTION

To improve upon prior systems and methods for monitoring foreshortening, the present disclosure provides inventions for detecting when and where foreshortening is occurring along the length of a shape-sensed device, and for managing an appropriate response to the detected foreshortening (e.g., reporting the foreshortening or recommending a repositioning of an imaging modality to alleviate the foreshortening).

One embodiment of the inventions of the present disclosure is an optical shape sensing ("OSS") foreshortening detection system employing an interventional device and an OSS foreshortening detection device.

The interventional device includes an integration of an OSS sensor and one or more one interventional tool. The OSS sensor is operable to generate shape sensing data informative of a shape of the OSS sensor.

The OSS foreshortening detection device includes an OSS shape controller for controlling a reconstruction of a shape of a portion or an entirety of the interventional device derived from a generation of the shape sensing data by the OSS sensor.

The OSS foreshortening detection device further includes an OSS foreshortening controller for controlling a monitoring of any foreshortening of the interventional device within an image of the interventional device including the OSS foreshortening controller detecting a location of any occurrence of a foreshortening of the interventional device within the image of interventional device derived from the reconstruction of the shape of the portion or the entirety of the interventional device by the OSS shape controller.

A second embodiment of the inventions of the present disclosure is the OSS foreshortening device employing the OSS shape controller and the OSS foreshortening controller.

A third embodiment of the inventions of the present disclosure is an OSS foreshortening detection method involving an OSS sensor generating shape sensing data informative of a shape of the OSS sensor.

The OSS foreshortening detection method further involves an OSS shape controller controlling a reconstruction of a shape of a portion or an entirety of the interventional device derived from a generation of the shape sensing data by the OSS sensor.

The OSS foreshortening detection method further involves an OSS foreshortening controller controlling a monitoring of any foreshortening of the interventional device within an image of the interventional device, including the OSS foreshortening controller detecting a location of any occurrence of a foreshortening of the interventional device within the image of interventional device derived from the reconstruction of the shape of the portion or the entirety of the interventional device by the OSS shape controller.

For purposes of describing and claiming the inventions of the present disclosure:

(1) terms of the art of the present disclosure including, but not limited to, "imaging modality" and "registration" are to be interpreted as known in the art of the present disclosure and exemplary described herein;

(2) the term "anatomical region" broadly encompasses, as known in the art of the present disclosure and exemplary described in the present disclosure, one or more anatomical systems with each anatomical system having a natural or a surgical structural configuration for a navigation of an interventional device therein. Examples of an anatomical region includes, but is not limited to, an integumentary system (e.g., skin and appendages), a skeletal system, a muscular system, a nervous system, an endocrine system (e.g., glands and pancreas), a digestive system (e.g., stomach, intestines, and colon), a respiratory system (e.g., airways and lungs), a circulatory system (e.g., heart and blood vessels), a lymphatic system (e.g., lymph nodes), a urinary system (e.g., kidneys), and reproductive system (e.g., uterus);

(3) the term "interventional tool" is to be broadly interpreted as known in the art of the present disclosure including interventional tools known prior to and conceived after the present disclosure. Examples of an interventional tool include, but are not limited to, vascular interventional tools (e.g., guidewires, catheters, stents sheaths, balloons, atherectomy catheters, IVUS imaging probes, deployment systems, etc.), endoluminal interventional tools (e.g., endoscopes, bronchoscopes, etc.) and orthopedic interventional tools (e.g., k-wires and screwdrivers);

(4) the term "OSS sensor" broadly encompasses an optical fiber structurally configured, as known in the art of the present disclosure and hereinafter conceived, for extracting high density strain measurements of the optical fiber derived from light emitted into and propagated through the optical fiber and reflected back within the optical fiber in an opposite direction of the propagated light and/or transmitted from the optical fiber in a direction of the propagated light. An example of an OSS sensor includes, but is not limited to, an optical fiber structurally configured under the principle of Optical Frequency Domain Reflectometry (OFDR) for extracting high density strain measurements of the optical fiber derived from light emitted into and propagated through the optical fiber and reflected back within the optical fiber in an opposite direction of the propagated light and/or transmitted from the optical fiber in a direction of the propagated light via controlled grating patterns within the optical fiber (e.g., Fiber Bragg Grating), a characteristic backscatter of the optical fiber (e.g., Rayleigh backscatter) or any other arrangement of reflective node element(s) and/or transmissive node element(s) embedded, etched, imprinted, or otherwise formed in the optical fiber;

(5) the phrase "integration of an interventional tool and an OSS sensor" broadly encompasses any type of combining, adjoining, attaching, mounting, insertion, intermingling or otherwise integrating of an interventional tool and an OSS sensor into a an interventional device as understood in the art of the present disclosure and exemplary described. Examples of such an integration include, but are not limited to, a fixed insertion of an OSS sensor within a channel of a catheter and a guidewire incorporating an OSS sensor;

(6) the term "OSS foreshortening detection system" broadly encompasses, as known in the art of the present disclosure and hereinafter conceived, all foreshortening monitoring systems utilized in interventional procedures incorporating the inventive principles of the present disclosure for implementing optical shape sensing (OSS) technology to detect a location of any occurrence of foreshortening of an interventional device within an image of the interventional device;

(7) the term "OSS foreshortening method" broadly encompasses, as known in the art of the present disclosure and hereinafter conceived, all foreshortening monitoring methods utilized in interventional procedures incorporating the inventive principles of the present disclosure for implementing optical shape sensing (OSS) technology to detect a location of any occurrence of foreshortening of an interventional device within an image of the interventional device;

(8) the term "controller" broadly encompasses all structural configurations of an application specific main board or an application specific integrated circuit for controlling an application of various inventive principles of the present disclosure related to a detection of a location of an occurrence of a foreshortening of an interventional device within an image of the interventional device as subsequently exemplarily described in the present disclosure. The structural configuration of the controller may include, but is not limited to, processor(s), computer-usable/computer readable storage medium(s), an operating system, application module(s), peripheral device controller(s), interface(s), bus(es), slot(s) and port(s). The labels "OSS shape" and "OSS foreshortening" used herein for the term "controller" distinguishes for identification purposes a particular controller from other controllers as described and claimed herein without specifying or implying any additional limitation to the term "controller".

(9) the term "application module" broadly encompasses a component of an controller consisting of an electronic circuit and/or an executable program (e.g., executable software and/or firmware stored on non-transitory computer readable medium(s)) for executing a specific application. The labels "Shape Reconstruction", "Foreshortening Detector" and "Foreshortening Manager" used herein for the term "module" distinguishes for identification purposes a particular module from other modules as described and claimed herein without specifying or implying any additional limitation to the term "application module"; and

(10) the terms "signal", "data", and "command" broadly encompasses all forms of a detectable physical quantity or impulse (e.g., voltage, current, or magnetic field strength) as understood in the art of the present disclosure and as exemplary described in the present disclosure for communicating information and/or instructions in support of applying various inventive principles of the present disclosure as subsequently described in the present disclosure. Signal/data/command communication between components of the present disclosure may involve any communication method, as known in the art of the present disclosure and hereinafter conceived, including, but not limited to, signal/data/command transmission/reception over any type of wired or wireless medium/datalink and a reading of signal/data/command uploaded to a computer-usable/computer readable storage medium.

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

BRIEF DESCRIPTION OF THE DRAWINGS

FIGS. 2A-2C illustrates exemplary embodiments of an OSS sensor as known in the art of the present disclosure.

DETAILED DESCRIPTION OF THE PREFERRED EMBODIMENTS

Figure 1A:
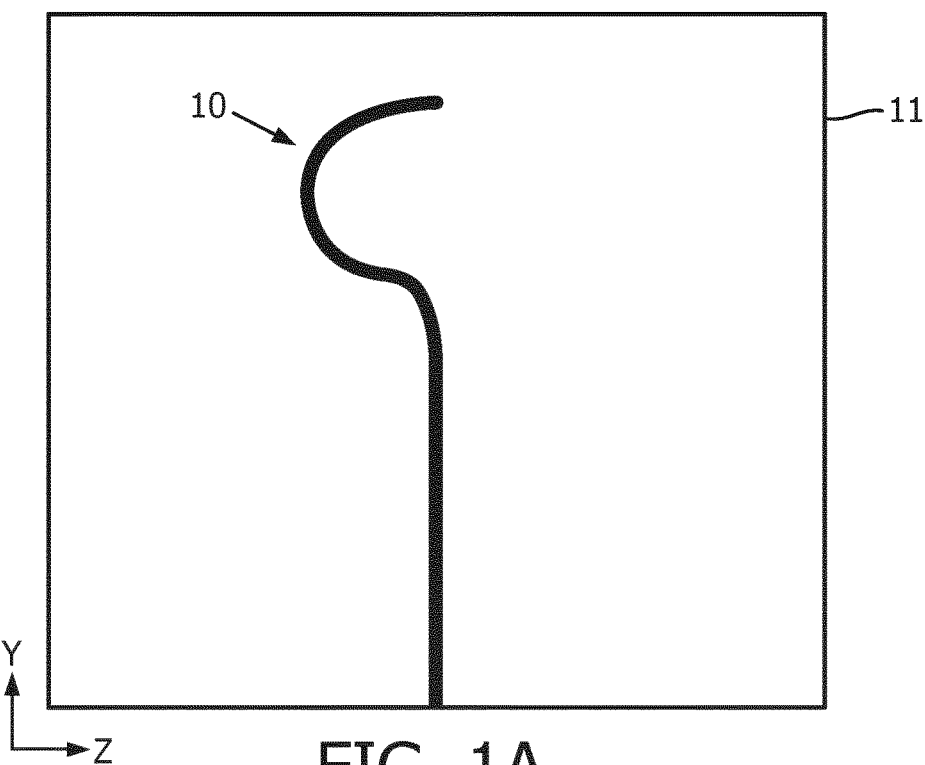
FIG. 1A illustrates an exemplary lateral projection of an X-ray image of an interventional device as known in the art of the present disclosure.
Figure 1B:
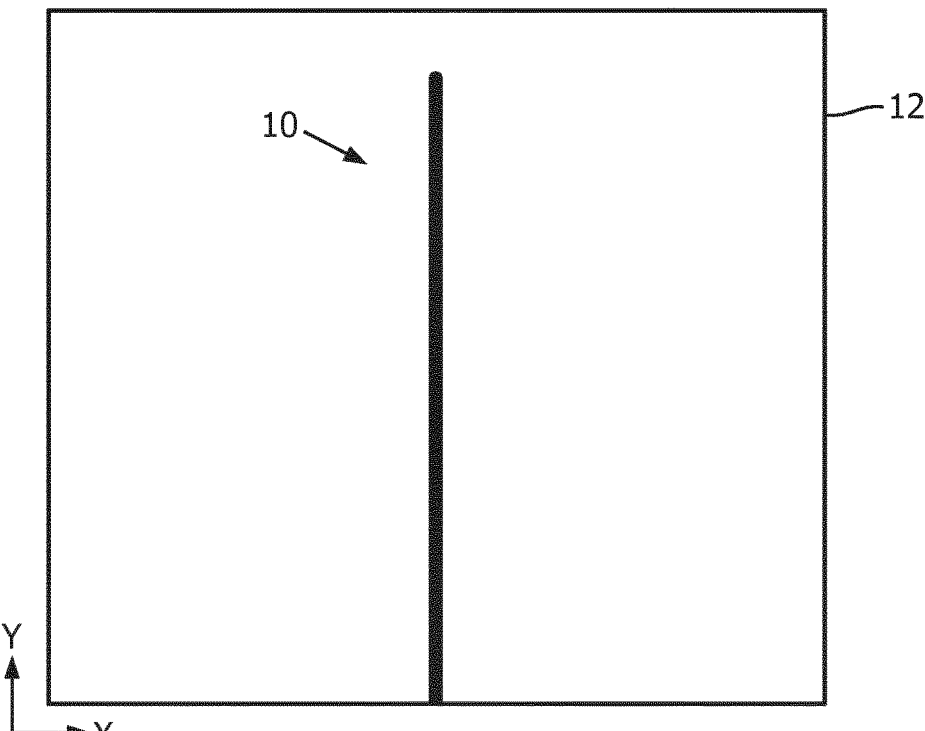
FIG. 1B illustrates an exemplary anteroposterior projection of an X-ray image of an interventional device as known in the art of the present disclosure.

As an improvement upon prior foreshortening monitoring systems, controllers and methods, the inventions of the present disclosure provide for detecting when and where foreshortening is occurring along the length of a shape-sensed device, and for managing an appropriate response to the detected foreshortening (e.g., reporting the foreshortening or recommending a repositioning of an imaging modality to alleviate the foreshortening).

To facilitate an understanding of the various inventions of the present disclosure, the following description of FIGS. 2A-5B teaches an interventional device having an integration of an interventional tool and an OSS sensor as known in the art of the present disclosure. From this description, those having ordinary skill in the art will appreciate various and numerous embodiments of an interventional device applicable to an OSS foreshortening detection of a navigation of the interventional device within an anatomical region in accordance with the inventive principles of the present disclosure. Please note the components of the present disclosure as shown in FIGS. 2A-5B are not drawn to scale, but drawn to conceptually support the inventive principles of the present disclosure.

Referring to FIG. 2A, an OSS sensor 20 applicable to the inventions of the present disclosure includes an optical fiber 21 as a single core optical fiber (e.g., a an optical fiber 21a having a single core 22 as shown in FIG. 2B) or a multi-core optical fiber (e.g. a multi-core optical fiber 21b having multi-cores 22b-22d as shown in FIG. 2C). A core of optical fiber 21 has controlled grating patterns (e.g., Fiber Bragg Gratings), a characteristic backscatter (e.g., Rayleigh backscatter) or any other arrangement of reflective elements and/or transmissive elements embedded, etched, imprinted, or otherwise formed in optical fiber 21. In practice, OSS nodes in the form of controlled gratings, characteristic backscatter, or reflective/transmissive elements may extend along any segment or an entirety of optical fiber 21 as symbolically shown by dashed line 22 extending from a proximal end 21p to a distal end 21d. Also in practice, OSS sensor 20 may include two (2) or more individual optical fibers 21 that may or may not be helixed.

In practice, optical fiber 21 of OSS sensor 20 may be made partially or entirely of any glass, silica, phosphate glass or other glasses, or made of glass and plastic or plastic, or other materials used for making optical fibers. For impeding any damage to OSS sensor 20 when introduced into a patient anatomy via manual or robotic insertion, an optical fiber 21 of OSS sensor 20 may permanently encircled by a protective sleeve as known in the art.

In practice, the protective sleeve may be made from any flexible material of a specified hardness including, but not limited to, pebax, nitinol, furcation tubing, and stranded metal tubing. Also in practice, the protective sleeve may consist of two or more tubular components of same or different degrees of flexibility and hardness in an overlapping and/or sequential arrangement.

OSS sensor 20 may further includes an optical connector 23 for connecting optical fiber 21 to another optical fiber, a launch or an optical source (e.g., optical integrator) as will be further described in the present disclosure.

Figure 3:
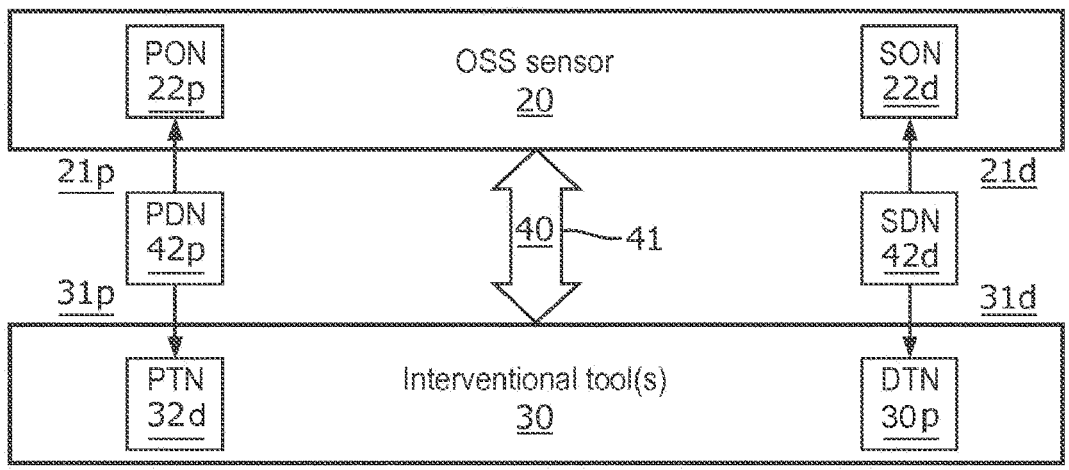
FIG. 3 illustrates an exemplary embodiment of an interventional device as known in the art of the present disclosure.

Referring to FIG. 3, the inventions of the present disclosure are premised on an integration of an OSS sensor 20 and one or more interventional tools 30 to configure an interventional device 40 for an execution of an interventional procedure involving a navigation of interventional device 40 within one or more anatomical regions (e.g., a heart and blood vessels of cardiovascular system, airways and lungs of a respiratory system, a stomach and intestines of a digestive system, and bores within of a musculoskeletal system).

Examples of interventional tool 30 include, but are not limited to, vascular interventional tools (e.g., guidewires, catheters, stents sheaths, balloons, atherectomy catheters, IVUS imaging probes, deployment systems, etc.), endoluminal interventional tools (e.g., endoscopes, bronchoscopes, etc.) and orthopedic interventional tools (e.g., k-wires and screwdrivers).

In practice, an integration of OSS sensor 20 and interventional tool 30 may be in any configuration suitable for a particular interventional procedure.

Further in practice, a proximal device node 42p of interventional device 40 may be a proximal OSS node 22p of OSS sensor 20. Alternatively, proximal device node 42p of interventional device 40 may be a proximal tool node 32p mapped to proximal OSS node 22p of OSS sensor 20 via a mechanical relationship mapping or a shape template based mapping between proximal OSS node 22p and proximal tool node 32p as known in the art of the present disclosure.

Similarly in practice, a distal device node 42d of interventional device 40 may be a distal OSS node 22d of OSS sensor 20. Alternatively, distal device node 42d of interventional device 40 may be a distal tool node 32d mapped to distal OSS node 22d of OSS sensor 20 via a mechanical relationship mapping or a shape template based mapping between distal OSS node 22d and distal tool node 32d as known in the art of the present disclosure.

Figure 4A:
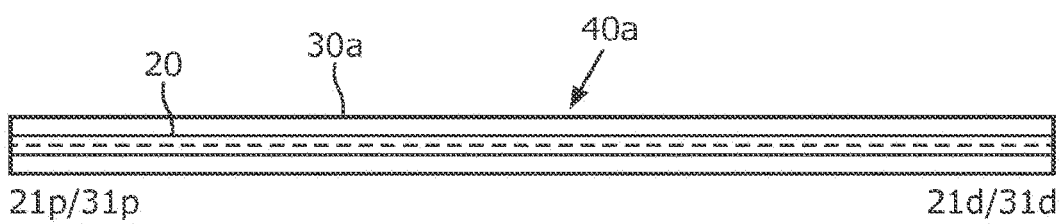
FIGS. 4A and 4B illustrate exemplary embodiments of an integration of an OSS sensor into a guidewire as known in the art of the present disclosure.
Figure 4B:
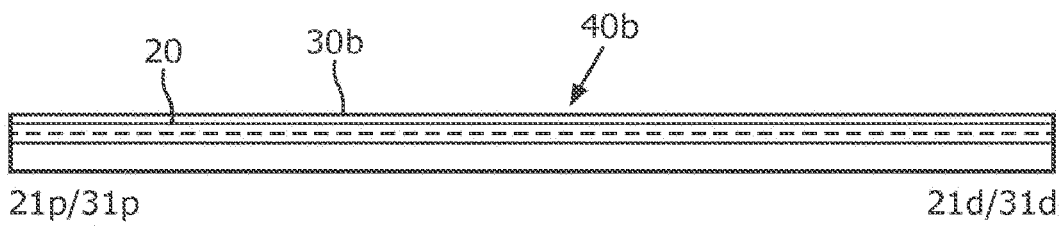

For example, FIG. 4A illustrates an OSS sensor 20 axially embedded within a guidewire 30a to configure an interventional device 40 in the form of an OSS guidewire 40a as known in the art of the present disclosure, and FIG. 4B illustrates OSS sensor 20 non-axially embedded within a guidewire 30b to configure an interventional device 40 in the form of an OSS guidewire 40b as known in the art of the present disclosure. OSS guidewire 40a and OSS guidewire 40b may be incorporated into any interventional procedure involving the utilization of a guidewire whereby the OSS guidewire 40a and OSS guidewire 40b may be navigated as necessary within anatomical region via a shape reconstruction capabilities of OSS sensor 20 as known in the art of the present disclosure.

Figure 5A:
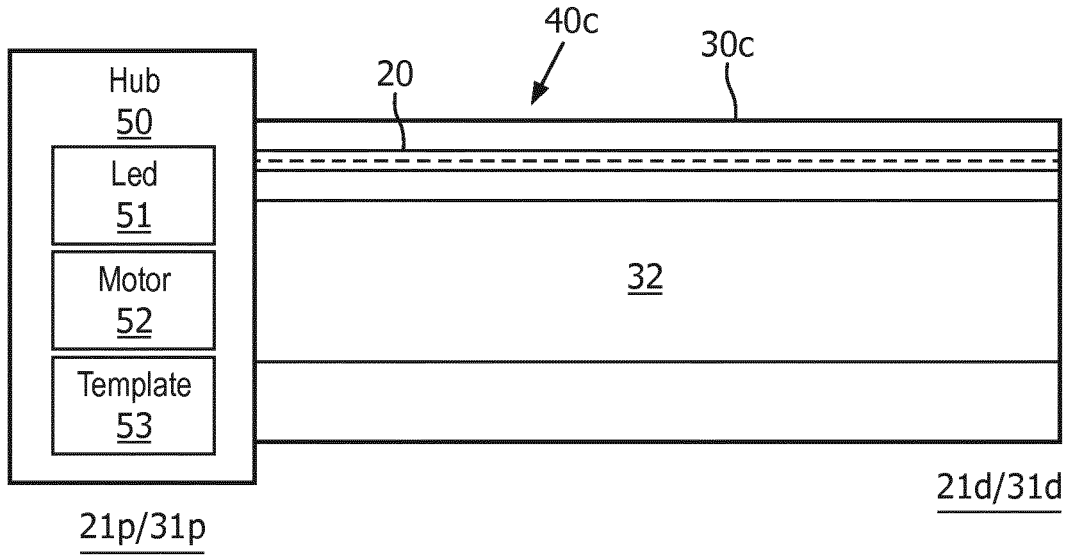
FIGS. 5A and 5B illustrate exemplary embodiments of an integration of an OSS sensor into catheter as known in the art of the present disclosure.

By further example, FIG. 5A illustrates an OSS sensor 20 temporarily or permanently inserted within a channel of a catheter 30c to configure an interventional device 40 in the form of a universal catheter 40c as known in the art of the present disclosure, and FIG. 4B illustrates an OSS guidewire 40b (FIG. 4B) temporarily or permanently inserted within a channel of catheter 30c to configure an interventional device 40 in the form of a universal catheter 40d as known in the art of the present disclosure. Universal catheter 40c and universal catheter 40d may be incorporated into any interventional procedure involving the utilization of a working channel 31c of catheter 30c whereby universal catheter 40c and universal catheter 40d may be navigated as necessary within anatomical region(s) via a shape reconstruction capabilities of OSS sensor 20 as known in the art of the present disclosure.

Figure 5B:
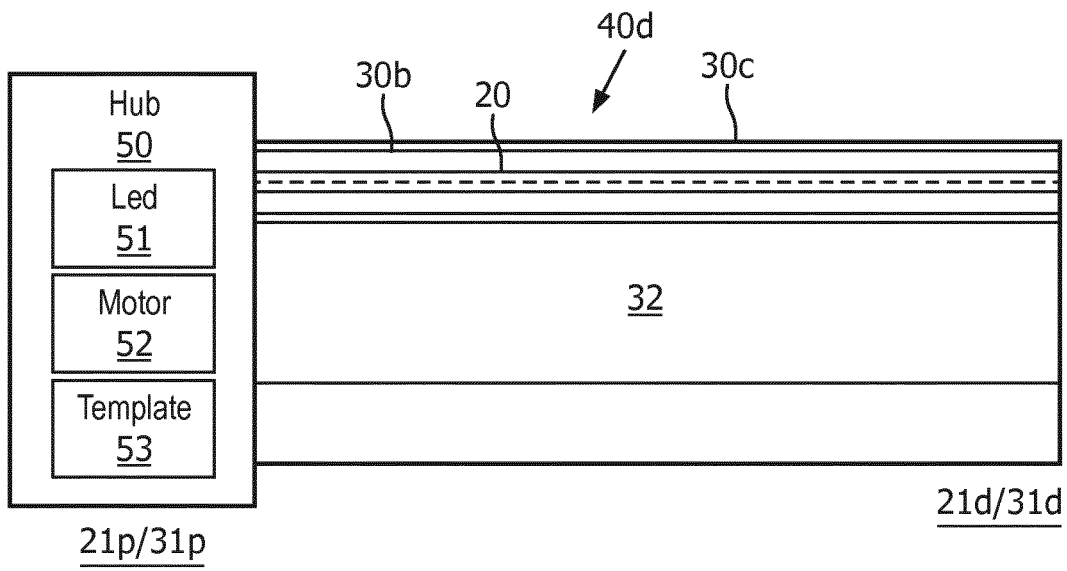

Still referring to FIGS. 5A and 5B, universal catheter 40c and universal catheter 40d may further employ a hub 51 for facilitating a navigation of universal catheter 40c and universal catheter 40d within anatomical regions as known in the art of the present disclosure. As will be further described in the present disclosure, in practice, hub 51 may include a light emitting diode (not shown in FIGS. 5A-5B) for providing visual feedback of an OSS monitoring of an interventional device attached to hub 51 in accordance with the inventive principles of the present disclosure, a vibrating motor 52 for providing haptic feedback of the OSS monitoring of an interventional device attached to hub 51 in accordance with the inventive principles of the present disclosure and/or an orientation template 53 for facilitating a generation of a torquability metric of an interventional device attached to hub 51 in accordance with the inventive principles of the present disclosure.

Referring back to FIG. 3, while proximal OSS node 22p is shown as being located within a proximal end 21p of OSS sensor 20 and distal OSS node 22d is shown as being located within a distal end 21d of OSS sensor 20, in practice proximal OSS node 22p and distal OSS node 22d may be located anywhere within the configuration of OSS sensor 20 limited only by a location of proximal OSS node 22p being closer to proximal end 21p of OSS sensor 20 than a location of distal OSS node 22d.

Similarly, while proximal tool node 32p is shown as being located within a proximal end 31p of interventional tool 30 and distal tool node 32d is shown as being located within a distal end 31d of interventional tool 30, in practice proximal tool node 32p and distal tool node 32d may be located anywhere within the configuration of interventional tool 30 limited only by a location of proximal tool node 32p being closer to proximal end 31p of interventional tool 30 than a location of distal tool node 32d.

More particularly, referring to FIGS. 4A and 4B, both OSS guidewire 40a and OSS guidewire 40b have a proximal device node (not shown) (e.g., proximal device node 41p of FIG. 3) and a distal device node (not shown) (e.g., a distal device node 41 of FIG. 3) located between a proximal end 21p/31p and a distal end 21d/31d as designated for a particular interventional procedure. For example, a proximal device node may be located at or adjacent a proximal origin of OSS guidewire 40a and a distal device node at or adjacent a distal tip of OSS guidewire 40a. Similarly, a proximal device node may be located at or adjacent a proximal origin of OSS guidewire 40b and a distal device node at or adjacent a distal tip of OSS guidewire 40b.

Further, referring to FIGS. 5A and 5B, both universal catheter 40c and universal catheter 40d have a proximal device node (not shown) (e.g., proximal device node 41p of FIG. 3) and a distal device node (not shown) (e.g., a distal device node 41 of FIG. 3) located between a proximal end 21p/31p and a distal end 21d/31d as designated for a particular interventional procedure. For example, a proximal device node may be located at or adjacent hub 51 of universal catheter 40c and a distal device node at or adjacent a distal tip of universal catheter 40c. Similarly, a proximal device node may be located at hub 51 of universal catheter 40d and a distal device node at or adjacent a distal tip of universal catheter 40d.

Figure 6:
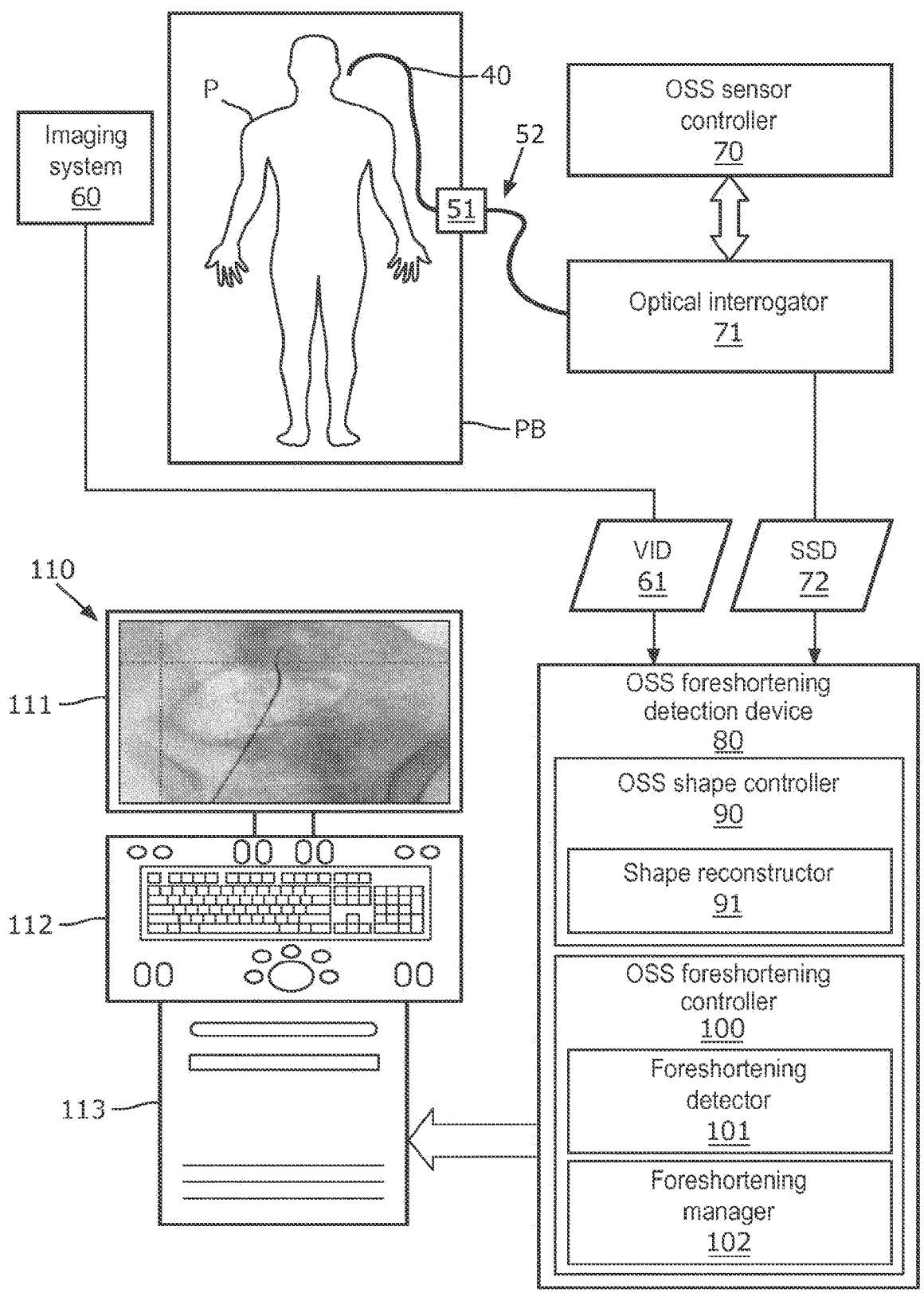
FIG. 6 illustrates an exemplary embodiment of an OSS foreshortening detection system in accordance with the inventive principles of the present disclosure.
Figure 7:
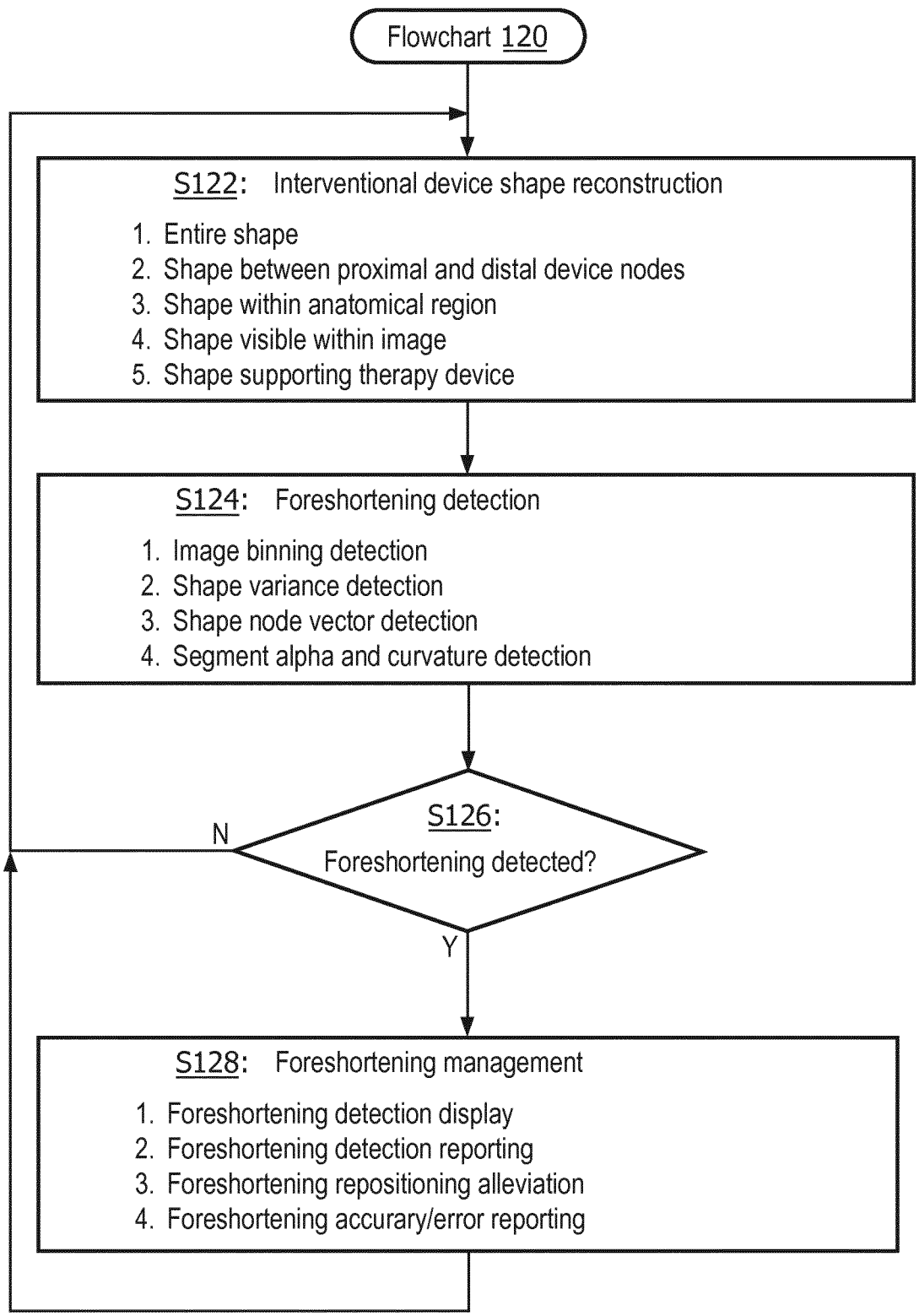
FIG. 7 illustrates an exemplary embodiment of an OSS foreshortening detection system in accordance with the inventive principles of the present disclosure.

To facilitate a further understanding of the inventions of the present disclosure, the following description of FIGS. 6 and 7 teaches basic inventive principles of OSS foreshortening detection systems, controllers and methods for detecting when and where foreshortening is occurring along the length of a shape-sensed device, and for managing an appropriate response to the detected foreshortening (e.g., reporting the foreshortening or recommending a repositioning of an imaging modality to alleviate the foreshortening). From this description of FIGS. 6 and 7, those having ordinary skill in the art will appreciate how to apply the inventive principles of the present disclosure to practice numerous and various embodiments of OSS foreshortening detection systems, controllers and methods in accordance with the inventive principles of the present disclosure.

Referring to FIG. 6, an OSS foreshortening detection system of the present disclosure employs an interventional device 40 (FIG. 2), an imaging system 60 and an OSS foreshortening detection device 80 including an OSS shape controller 90 and an OSS foreshortening controller 100 installed on a workstation 110. The OSS foreshortening detection system provides a detection of any folding and any twisting of interventional device 40 within anatomical region(s) of a patient P lying prone or otherwise on a patient bed PB (e.g., a heart and blood vessels of cardiovascular system, airways and lungs of a respiratory system, a stomach and intestines of a digestive system, and bores within of a musculoskeletal system).

In practice, interventional device 40 includes an integration of an interventional an OSS sensor 20 and one or more interventional tool(s) 30 as previously described in the present disclosure in connection with FIGS. 2-5B. For example, interventional device 40 may be OSS guidewire 40a (FIG. 4A), OSS guidewire 40b (FIG. 4B), universal catheter 40c (FIG. 5A) and universal catheter 40d (FIG. 5B).

In practice, imaging system 60 may implement any type of imaging modality for generating a volume image(s) of anatomical region(s) of patient P (e.g., an X-ray system, a MRI system, a CT system, an ultrasound system, etc.).

In practice, OSS shape controller 90 and OSS foreshortening controller 100 may embody any arrangement of hardware, software, firmware and/or electronic circuitry for foreshortening detection a navigation of interventional device 40 within anatomical region(s) of patient P in accordance with the inventive principles of the present disclosure.

In one embodiment, OSS shape controller 90 and OSS foreshortening controller 100 may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The operator interface may include one or more devices, as known in the art of the present disclosure or hereinafter conceived, for enabling communication with a user such as an administrator. In a non-limiting example, the operator interface may include a command line interface or graphical user interface that may be presented to a remote terminal via the network interface.

The network interface may include one or more devices, as known in the art of the present disclosure or hereinafter conceived, for enabling communication with other hardware devices. In a non-limiting example, the network interface may include a network interface card (NIC) configured to communicate according to the Ethernet protocol. Additionally, the network interface may implement a Transmission Control Protocol/Internet Protocol (TCP/IP) stack for communication according to the TCP/IP protocols. Various alternative or additional hardware or configurations for the network interface will be apparent.

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules in the form of executable software/firmware.

More particularly, still referring to FIG. 6, an application module of OSS shape controller 90 is a shape reconstructor 91 for reconstructing a portion or an entirety of a shape of interventional device 40 in response to shape sensing data 72 as known in the art of the present disclosure and further exemplary described in the present disclosure.

Further, application modules of OSS foreshortening controller 100 include a foreshortening detector 101 for detecting any folding of interventional device 40 within anatomical region(s) of patient P in accordance with the inventive principles of the present disclosure as will be further exemplarily described in the present disclosure, and/or a foreshortening manager 102 for detecting any twisting of interventional device 40 within anatomical region(s) of patient P in accordance with the inventive principles of the present disclosure as will be further exemplarily described in the present disclosure.

In practice, OSS foreshortening controller 100 may include foreshortening detector 101 for detecting a location of an occurrence of a foreshortening of the interventional device 40 within the image of interventional device 40 whereby the foreshortening detection is derived from the reconstruction of the portion/entirety of a shape of interventional device by shape reconstructor 91 as will be further explained in the present disclosure.

Also in practice, OSS foreshortening controller 100 may include foreshortening manager 102 for managing an appropriate response to a detection of the location of the occurrence of the foreshortening of interventional device 40 within the image of interventional device 40 in the present disclosure.

Still referring to FIG. 6, workstation 110 includes a known arrangement of a monitor 111, a keyboard 112 and a computer 113.

In practice, OSS foreshortening detection device 80 may be alternatively or concurrently installed on other types of processing devices including, but not limited to, a tablet or a server accessible by workstations and tablets, or may be distributed across a network supporting an execution of interventional procedures involving interventional device 40.

Also in practice, OSS shape controller 90 and OSS foreshortening controller 100 may be integrated components, segregated components or logically partitioned components of OSS foreshortening detection device 80.

Still referring to FIG. 6, in operation, imaging system 60 pre-operatively and/or intra-operatively generates volume image data VID 61 for displaying a volume image of the subject anatomical region(s) of patient P. Volume image data VID 61 is communicated to OSS foreshortening detection device 80 (e.g., a streaming or an uploading of volume image data VID 61) whereby OSS shape controller 90 may control an overlay display of a reconstructed shape of interventional device 40 on the volume image of anatomical region(s) of patient P as known in the art of the present disclosure. For example, FIG. 6 illustrates an overlay display on monitor 111 of a reconstructed shape of interventional device 40 on a volume image of vasculature of patient P.

Interventional device 40 distally extends from 51 adjoined to a rail of patient bed PB as shown, or alternatively adjoined to a cart (not shown) next to patient bed PB or alternatively adjoined to a workstation (e.g., workstation 110 or a tablet (not shown)). An optical fiber 52 proximally extends from launch 51 to an optical interrogator 71. In practice, optical fiber 52 may be a separate optical fiber connected to OSS sensor 20 of interventional device 40 at launch 51, or a proximal extension of OSS sensor 20 extending through launch 51.

As known in the art of the present disclosure, an OSS sensor controller 70 controls a cyclical emission of light by optical interrogator 71 via optical fiber 52 into OSS sensor 20 whereby the light is propagated through OSS sensor 20 to a distal tip of interventional device 40 to thereby generate shape sensing data 72 informative of a shape of interventional device 40 relative to launch 51 serving as a fixed reference position. In practice, the distal end of OSS sensor 20 may be closed, particularly for light reflective embodiments of OSS sensor 20, or may be opened, particularly for light transmissive embodiments of OSS sensor 20.

OSS sensor controller 70 controls a communication of a temporal frame sequence of shape sensing data 72 to OSS shape controller 90 as known in the art of the present disclosure. More particularly, each frame consists of a single interrogation cycle of the strain sensors of OSS sensor 20 (e.g., Fiber Bragg Gratings or Rayleigh backscatter) whereby shape reconstructor 91 reconstructs a shape of OSS sensor 20 on a temporal frame basis as known in the art of the present disclosure, which provides for a reconstruction of a portion or an entirety of the shape of interventional device 40 derived from the particular integration of OSS sensor 20 and interventional device(s) 30.

In practice, shape reconstructor 91 may implement any reconstruction technique for reconstructing the portion/entirety of a shape of interventional device 40 as known in the art of the present disclosure.

In one reconstruction embodiment, shape reconstructor 91 executes a delineation of pose of the portion/entirety of a shape of interventional device 40 via shape sensing data 72 on a temporal frame basis within a coordinate system corresponding to optical interrogator 71.

In a second reconstruction embodiment, shape reconstructor 91 executes a registration of a coordinate system of optical interrogator 71 to a coordinate system of imaging system 60 whereby shape reconstructor 91 may position and orientate a delineation of the portion/entirety of a shape of interventional device 40 via shape sensing data 72 on a temporal frame basis within the coordinate system of imaging system 60.

FIG. 7 illustrates a flowchart 120 representative of an OSS foreshortening detection method of the present disclosure that is implemented by the OSS foreshortening detection system of FIG. 6.

Referring to FIGS. 6 and 7, a stage S122 of flowchart 120 encompasses shape reconstructor 91 reconstructing a portion or an entirety of a shape of interventional device 40 in response to shape sensing data 72 as known in the art of the present disclosure.

Figure 8A:
FIGS. 8A-8E illustrate exemplary shape reconstructions of an interventional tool in accordance with the inventive principles of the present disclosure.
Figure 8B:
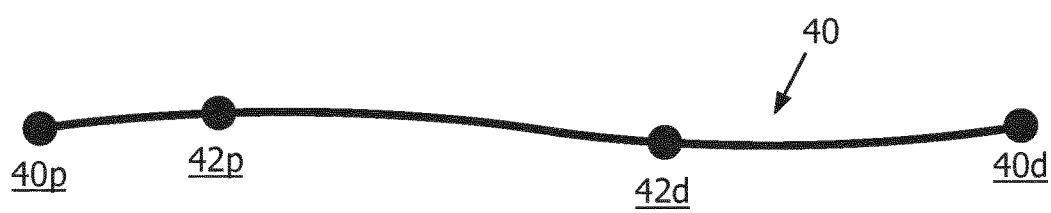

In one exemplary embodiment, as shown in FIG. 8A, shape reconstructor 91 may reconstruct an entire shape of interventional device 40 between a proximal end 40p and a distal end. For this example, interventional device 40 may be an OSS guidewire.

interventional device 40 between a proximal device node 42p and a distal device node 42d. For this example, interventional device 40 may employ an OSS guide wire extending between proximal end 40p and distal end 30d, and may further employ a hub catheter extending between proximal device node 42p and distal device node 42d.

Figure 8C:
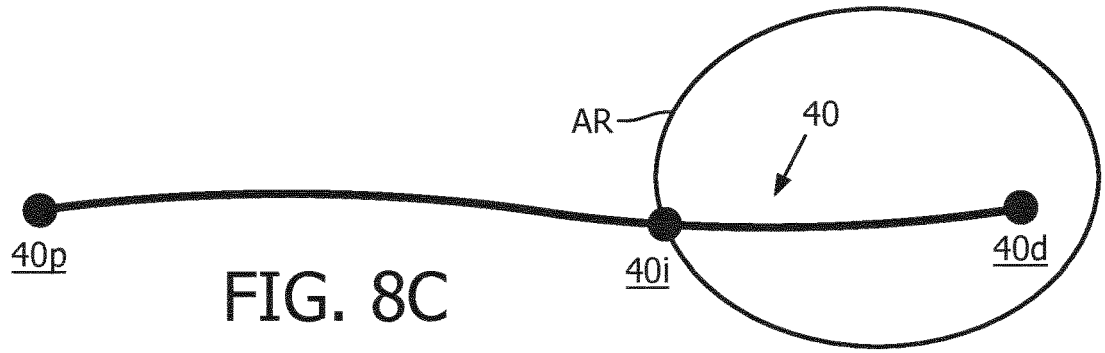

In a third exemplary embodiment, as shown in FIG. 8C, shape reconstructor 91 may reconstruct a portion of the interventional device 40 between an intermediate device node 40i and a distal device node 42d with intermediate device node 40i being identified as the node at the entry point of an anatomical region AR as known in the art of the present disclosure.

Figure 8D:
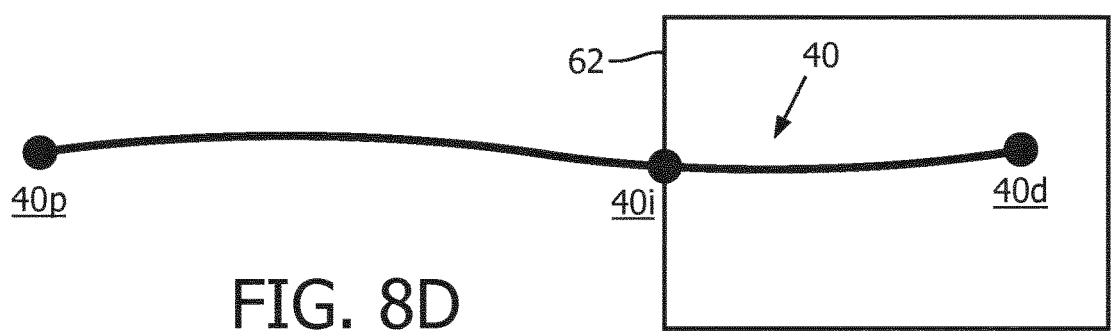

In a fourth exemplary embodiment, as shown in FIG. 8D, shape reconstructor 91 may reconstruct a portion of the interventional device 40 between an intermediate device node 40i and a distal device node 42d with intermediate device node 40i being identified as the node at the entry point of image 62 of interventional device 40 as known in the art of the present disclosure. For this embodiment, image 62 of interventional device 40 may be of interventional device 40 only for purpose of registering interventional device 40 to imaging modality 60, or of registered interventional device 40 within an anatomical region for purposes of visualizing an interventional procedure via monitor 111.

Figure 8E:
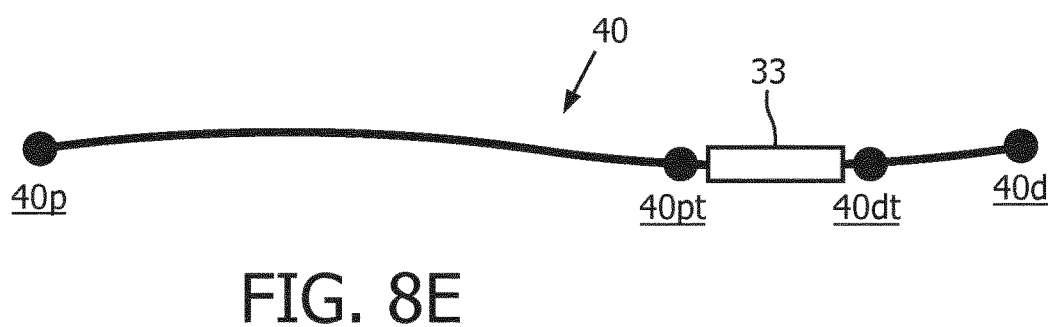

In a fifth exemplary embodiment, as shown in FIG. 8E, shape reconstructor 91 may reconstruct a portion of the interventional device 40 between a proximal tool node 40pt and a distal tool node 40dt enclosing an therapy device 33 (e.g., a balloon, a stent, an endograft, etc.).

Referring back to FIGS. 6 and 7, a stage S124 of flowchart 120 encompasses foreshortening detector 101 executing one or more routines for detecting a location of an occurrence of a foreshortening of interventional device 40 in the image of interventional device 40.

In one exemplary embodiment of S124, foreshortening detector 101 executes an image binning routine involving segmentation of the image of interventional device 40 into bins whereby each shape node of OSS sensor 20 is allocated to a bin. In practice, the image binning may be achieved by a M×M pixel segmentation, a M×N pixel segmentation, or a N×M pixel segmentation, where M≥1 and N≥1.

For this image binning routine, bin(s) having a highest number of shape nodes are candidates for foreshortening. If foreshortening detector 101 determines a particular planar view of interventional device 40 illustrates a shape of interventional device 40 indicative of a foreshortening of interventional device 40 within that planar view, then foreshortening detector 101 identifies the foreshortening candidate bin(s) as location(s) of an occurrence of a foreshortening of interventional device 40 in a corresponding image of interventional device 40.

Figure 9A:
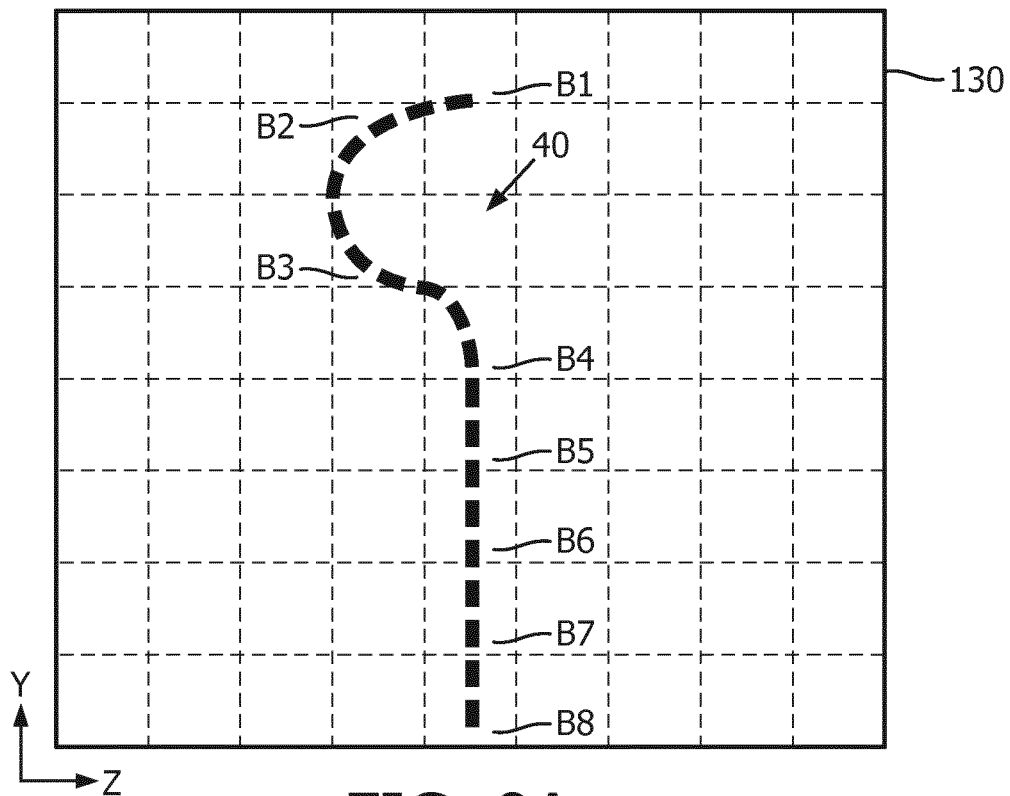
FIGS. 9A and 9B illustrate an exemplary imaging binning in accordance with the inventive principles of the present disclosure.
Figure 9B:
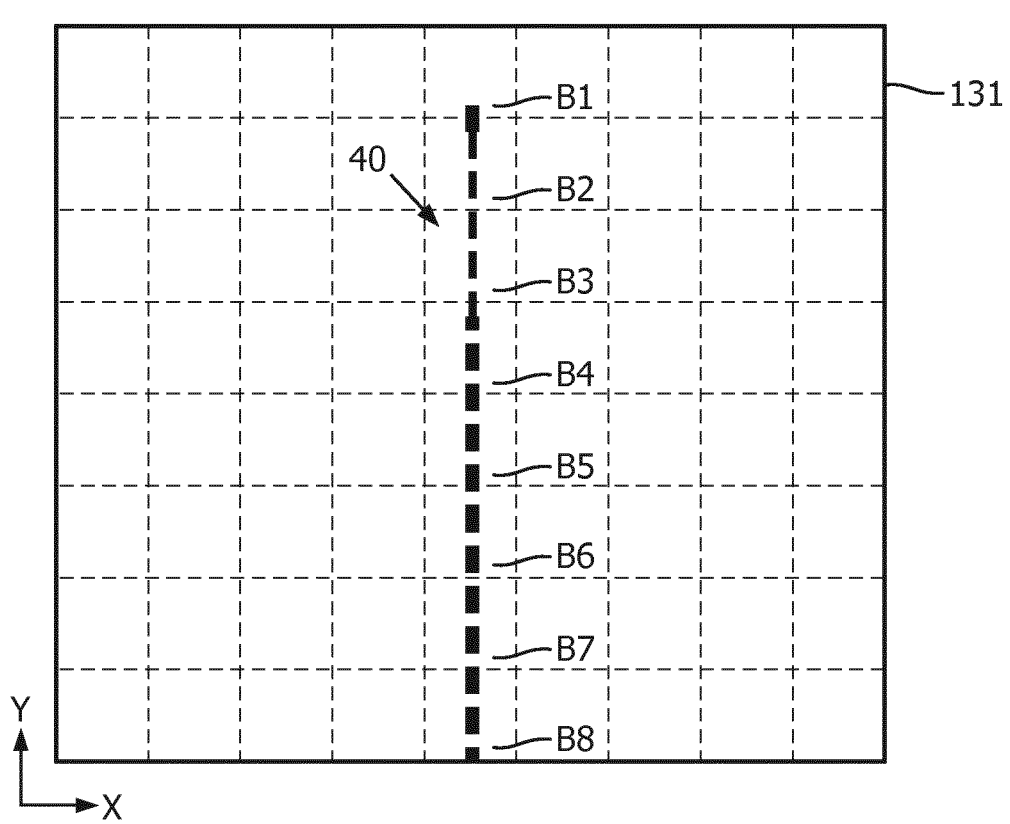

For example, FIGS. 9A and 9B illustrate a binning of respective images 130 and 131 of interventional device 40 into a 8×8 pixel segmentation. Bins B1 and B4-B8 contain no more than three (3) shape nodes while bins B2 and B3 contain four (4) shape nodes. As such, bins B2 and B3 are candidates for foreshortening. A shape of interventional device 40 is curvilinear in image 130 as shown in FIG. 9A, particularly curving at bins B2 and B2, and therefore foreshortening detector 101 would not detect any occurrence of a foreshortening of interventional device 40 within image 130. By comparison, a shape of interventional device 40 is linear in image 131 as shown in FIG. 9B, and foreshortening detector 101 therefore detects a foreshortening of interventional device 40 within image 131 at a location corresponding to bins B2 and B3.

Referring back to FIGS. 6 and 7, in a second exemplary embodiment of S124, foreshortening detector 101 executes a shape variance routine involving a computation of a shape variance along a reconstructed portion/entire shape of interventional device 40. In practice, foreshortening detector 101 may implement any type of shape variance routine as known in the art of the present disclosure including, but not limited to, a principle component analysis (PCA).
interventional device 40 having the highest shape variance are candidates for foreshortening in planar view(s) of a linear shape of interventional device 40. If foreshortening detector 101 determines a particular image of interventional device 40 illustrates a linear shape of interventional device 40, then foreshortening detector 101 identifies the segment(s) of the reconstructed portion/entire shape on interventional device 40 having the highest shape variance as location(s) of an occurrence of a foreshortening of interventional device 40 in that particular corresponding image of interventional device 40.

Figure 10A:
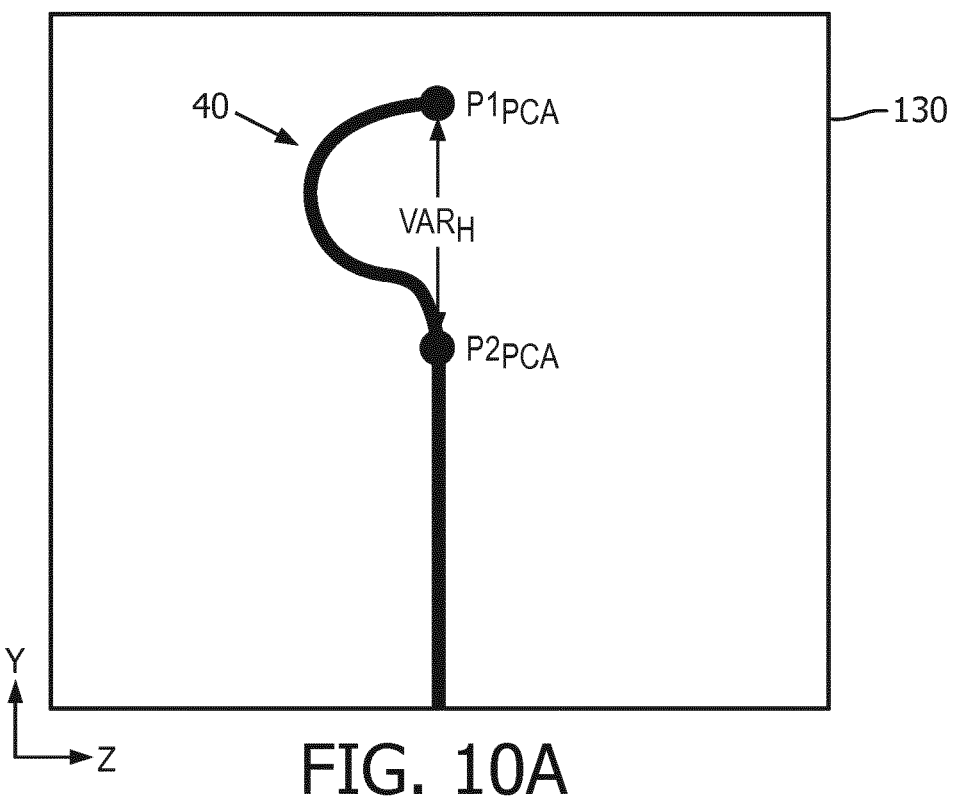
FIGS. 10A and 10B illustrate an exemplary shape variance computation in accordance with the inventive principles of the present disclosure.
Figure 10B:
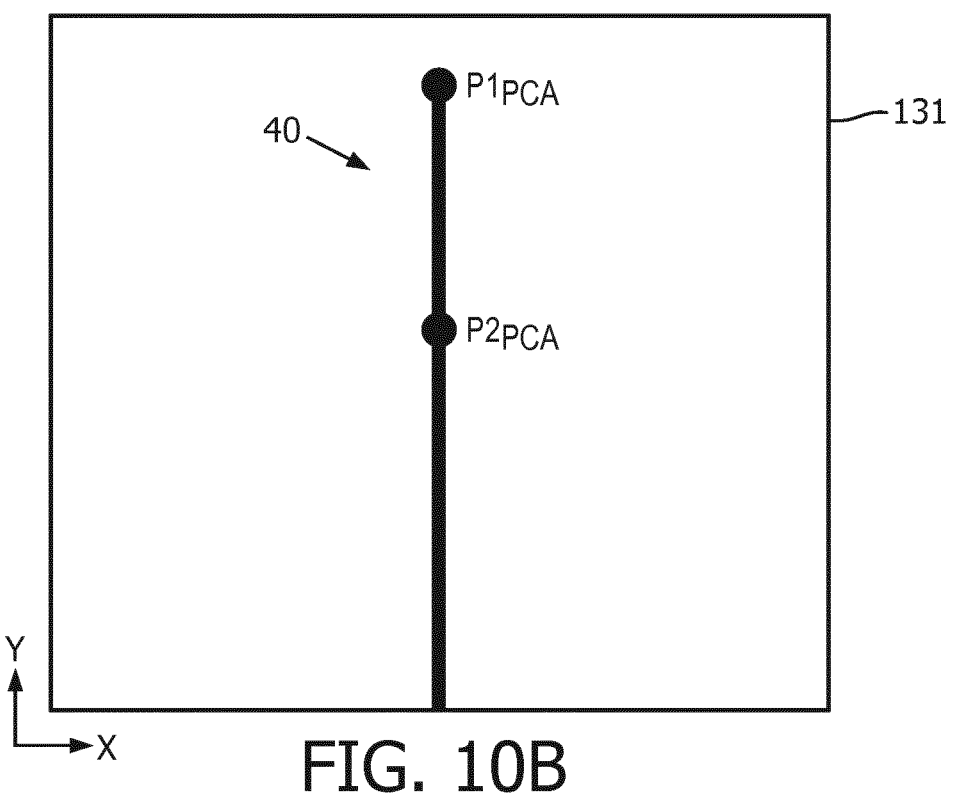

$P1_{PCA}$ and $P2_{PCA}$ having a highest shape variance $VAR_H$ and therefore, as shown in FIG. 10B, foreshortening detector 101 detects a foreshortening of a linear shape of interventional device 40 within image 131 at a location corresponding to the segment between shape nodes $P1_{PCA}$ and $P2_{PCA}$.

Referring back to FIGS. 6 and 7, in a third exemplary embodiment of S124, foreshortening detector 101 executes a shape node vector routine involving a computation of a vector each shape node of the shape of the reconstructed portion/entire shape of interventional device 40. For this shape node vector routine, segment(s) of shape nodes having the smallest magnitude in a same direction of the other vectors may are candidates for foreshortening in the image of interventional device 40.

Figure 11A:
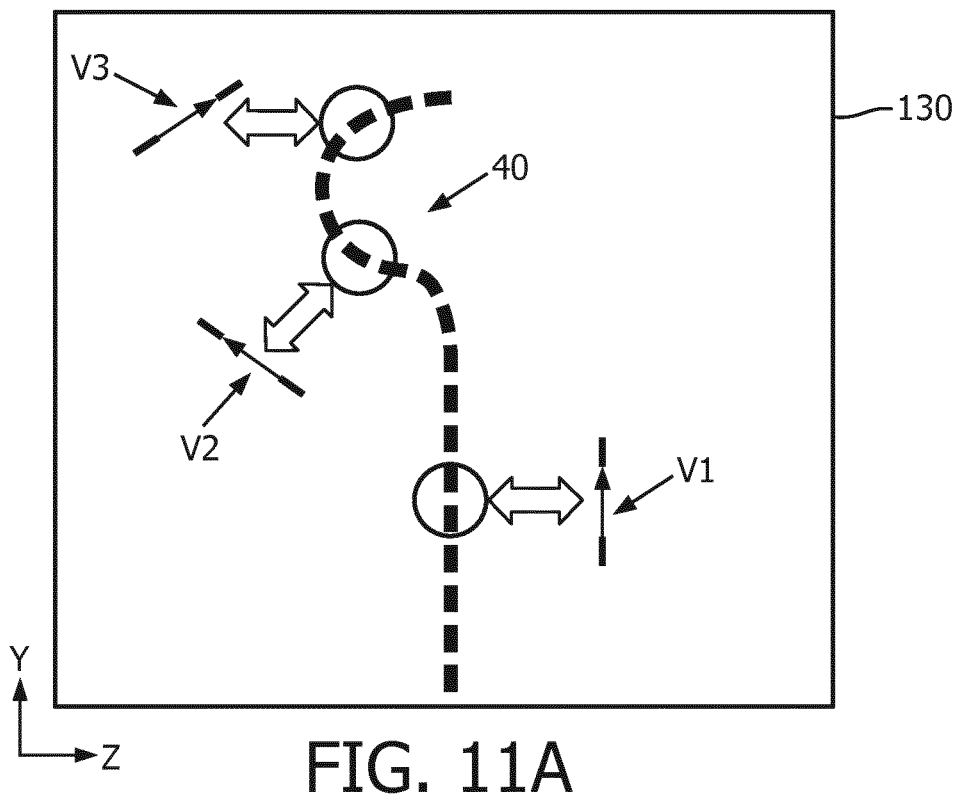
FIGS. 11A and 11B illustrate an exemplary node vector computation in accordance with the inventive principles of the present disclosure.
Figure 11B:
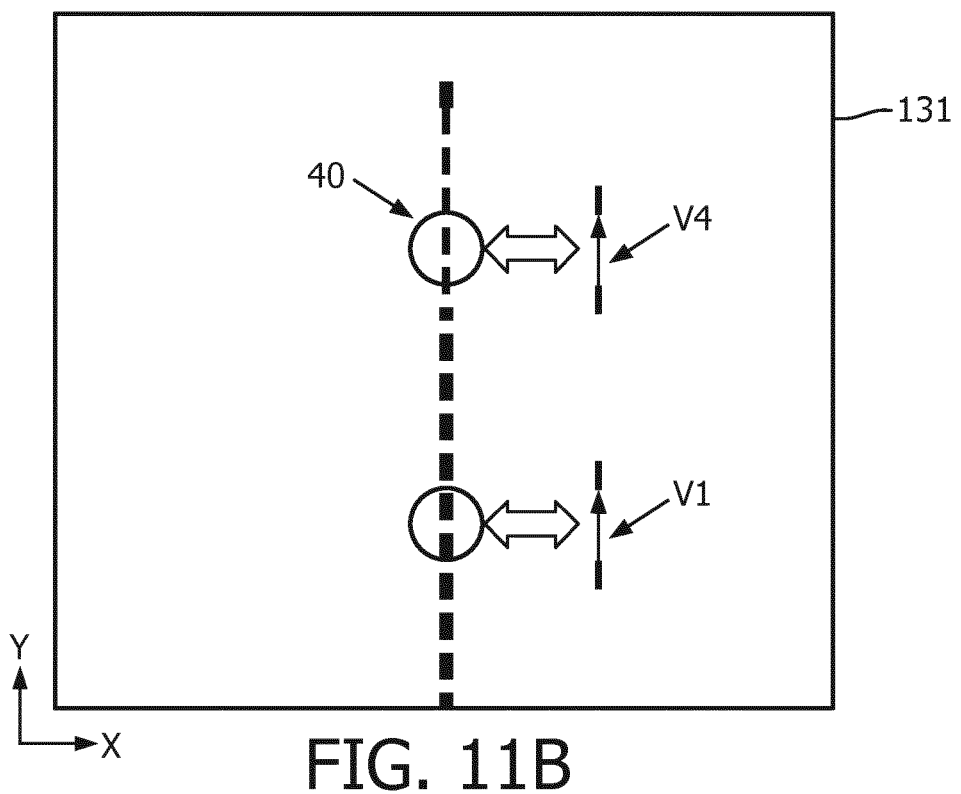

For example, FIG. 11A illustrates a computation of vectors V1, V2 and V3 having the same magnitude and different directions within image 130 of interventional device 40. Thus, foreshortening detector 101 would not detect a foreshortening of interventional device 40 within image 130. By comparison, FIG. 11B illustrates a computation of vectors V1 and V4 having different magnitude and same directions within image 131 of interventional device 40. Thus, foreshortening detector 101 would detect a foreshortening of interventional device 40 within image 130 of a segment at a location of vector V4 and equivalent adjacent vectors.

Referring back to FIGS. 6 and 7, in a fourth exemplary embodiment of S124, foreshortening detector 101 executes a segment alpha and curvature routine involving a computation of an alpha and a curvature along a reconstructed portion/entire shape of interventional device 40. In practice, foreshortening detector 101 may implement any type of alpha and curvature routine as known in the art of the present disclosure. interventional device 40 having the highest alpha/curvature are candidates for foreshortening in planar view(s) of a linear shape of interventional device 40. If foreshortening detector 101 determines a particular image of interventional device 40 illustrates a linear shape of interventional device 40, then foreshortening detector 101 identifies the segment(s) of the reconstructed portion/entire shape on interventional device 40 having the highest alpha/curvature as location(s) of an occurrence of a foreshortening of interventional device 40 in that particular corresponding image of interventional device 40.

Figure 12A:
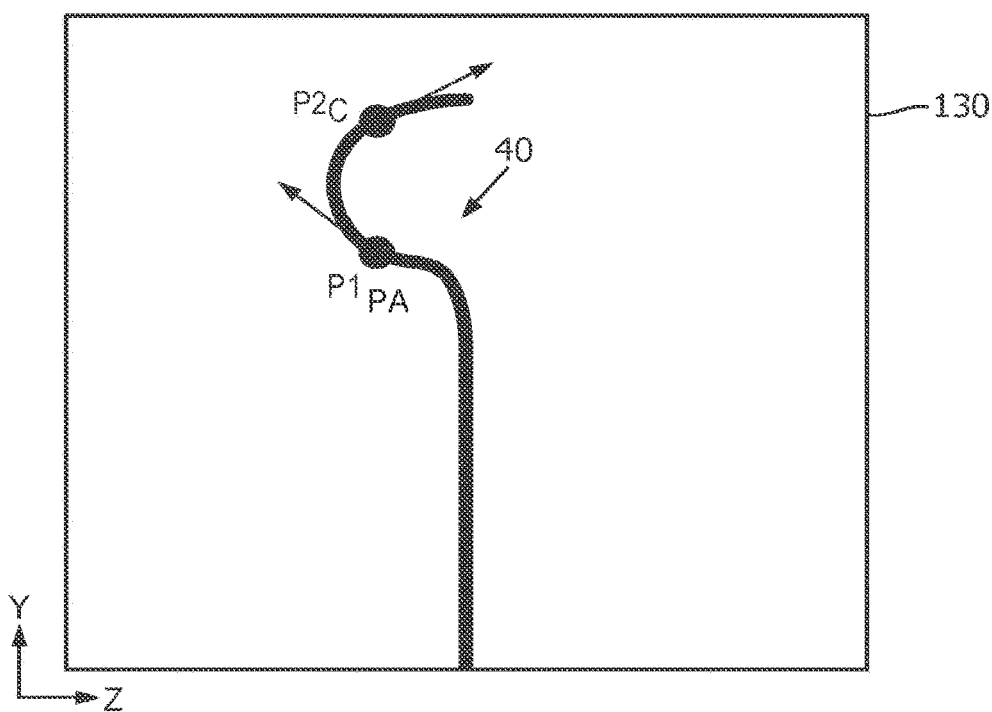
FIGS. 12A and 12B illustrate an exemplary alpha/curvature computation in accordance with the inventive principles of the present disclosure.
Figure 12B:
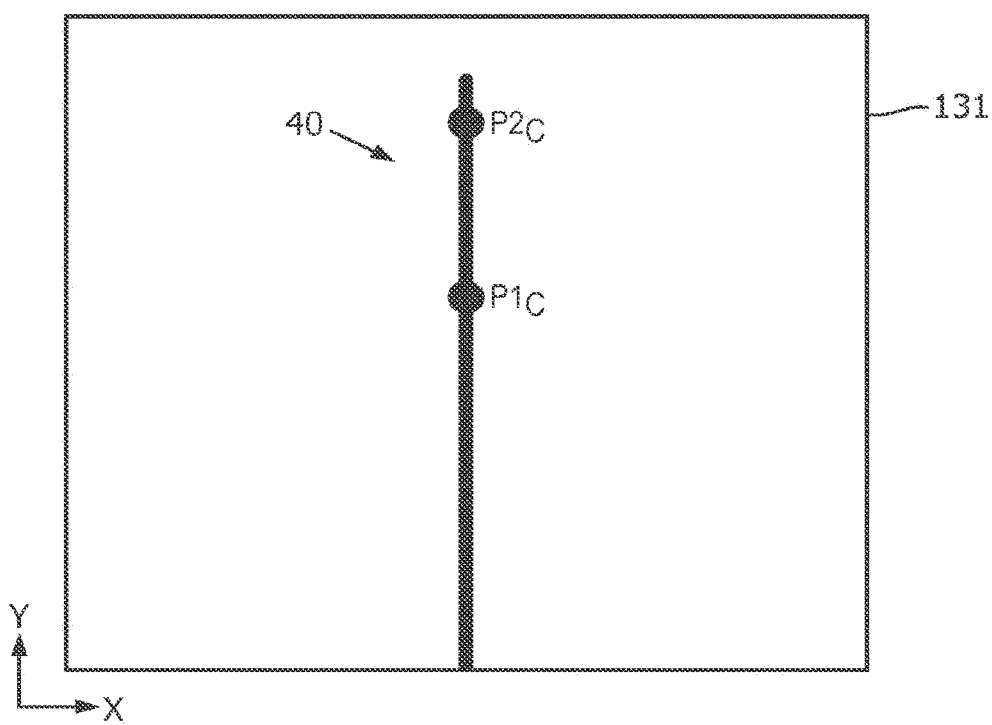

For example, FIG. 12A illustrate a segment between shape nodes $P1_{PA}$ and $P2_C$ having a highest shape variance $VAR_H$ and therefore, as shown in FIG. 12B, foreshortening detector 101 detects a foreshortening of a linear shape of interventional device 40 within image 131 at a location corresponding to the segment between shape nodes $P1_C$ and $P2_C$.

In practice, for any embodiment of stage S124, foreshortening detector 101 may ignore single node or any minimal node foreshortening deemed to be of zero relevance to a registration or navigation of interventional device 40.

Referring back to FIGS. 6 and 7, if foreshortening detector 101 does not detect a foreshortening within an image of interventional device 40 during stage S124, then foreshortening detector 101 returns from a stage S126 to stages S122 and S124 to execute a new cycle of shape reconstruction/foreshortening detection.

Otherwise, if foreshortening detector 101 does detect a foreshortening within an image of interventional device 40 during stage S124, then foreshortening detector 101 proceeds to a stage S128 to flowchart 120 where foreshortening manager 102 characterizes the detected foreshortening for the reconstructed portion/entire shape of interventional device 40 that may be communicated to an operator of the foreshortening detection system in a variety of ways.

Figure 13A:
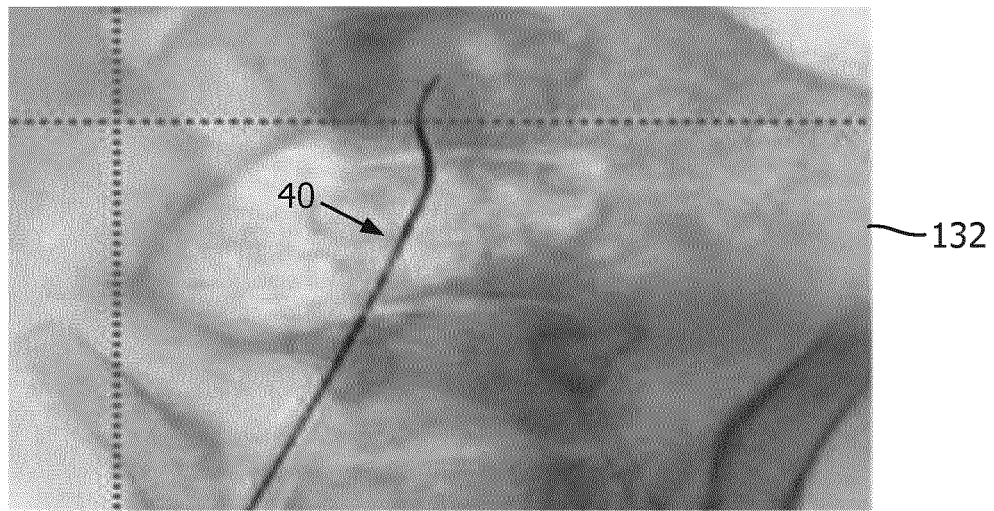
FIGS. 13A-13C illustrate an exemplary foreshortening warnings in accordance with the inventive principles of the present disclosure.
Figure 13B:
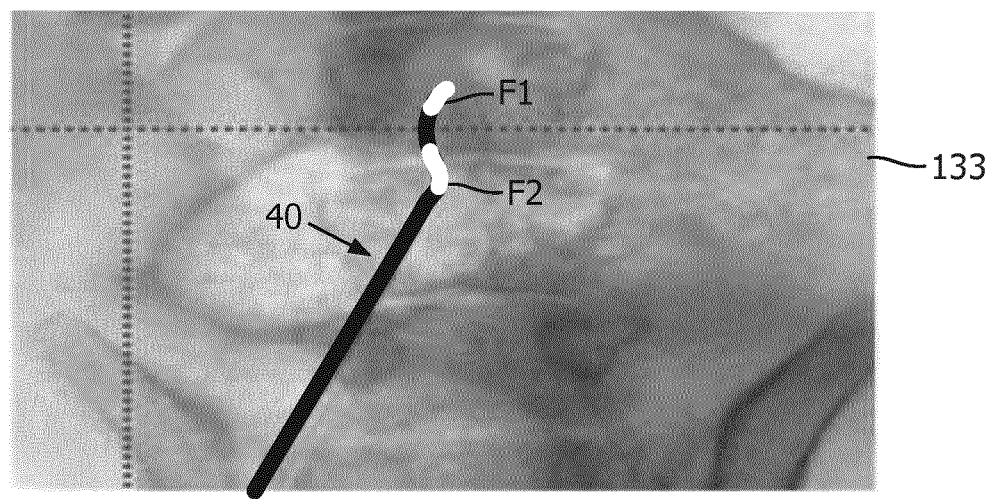
Figure 13C:
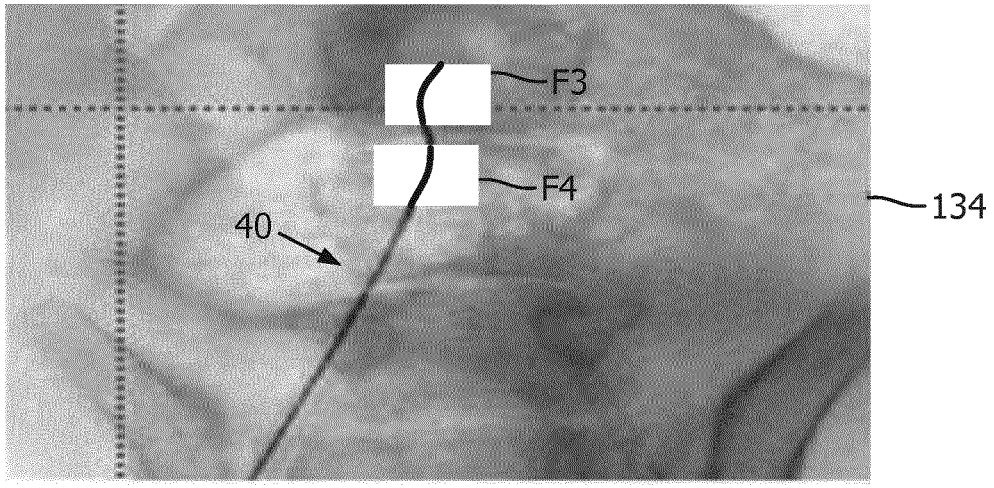

In one embodiment of stage S128, foreshortening manager 102 may manage a color coding of the detected foreshortening location. For example, FIG. 13A illustrates an X-ray image 132 of a navigation of a foreshortened interventional device 40 within an anatomical region as known in the art of the present disclosure with interventional device 40 being registered to the X-ray device. In accordance with the inventive principles of the present disclosure, FIG. 13B illustrates an X-ray image 133 of a navigation of a foreshortened interventional device 40 within an anatomical region with interventional device 40 being registered to the X-ray device and detected foreshortening locations F1 and F2 being color coded on interventional device 40. In practice, the color of the detected foreshortening locations and non-foreshortening locations of interventional device 40 may be any color (e.g., detected foreshortening locations may have a red with non-foreshortening locations being green). Further in practice, the color coding may involve a blinking of the detected foreshortening locations, a thickening of interventional device 40 at the detected foreshortening locations, or other changes to the shape display. More particularly, as to shape node vector embodiment, an amount of viewer component in each vector (e.g., z-component in each vector) may be used to color-code the detected foreshortening locations. This color coding can also be averaged across multiple nodes to make the visualization smoother. In a second embodiment of S128, foreshortening manager 102 may manage on overlay onto the detected foreshortening locations of interventional device 40. For example, as shown in FIG. 13C, overlays F3 and F4 are projected onto the detected foreshortening locations of interventional device 40 within an X-ray image 134. In practice, an overlay may also be blinking, have any geometric shape, be any icon or otherwise effect a notification change within the image.

In a third embodiment of stage S128, foreshortening manager 102 may issue an textual display and/or audible alert to the operator of the foreshortening detection system that foreshortening is occurring within the image at specific location(s).

In a fourth embodiment of stage S128, foreshortening manager 102 may suggest a repositioning of an imaging modality to alleviate any foreshortening of interventional device 40. For example, with an X-ray modality, foreshortening manager 102 may suggest a repositioning of a c-arm position to avoid foreshortening. In the case where there is an entire shape with multiple sections that may or may not have foreshortening, the operator of the foreshortening detection system could click on the section of the shape (or the overlayed region) and the c-arm could automatically move the optimal position to view that segment of shape.

In a fourth embodiment of stage S128, foreshortening manager 102 may display a registration accuracy and/or a registration error as will be further described in the present disclosure.

Still referring to FIGS. 6 and 7, in practice, foreshortening manager 102 may enable an operator of the foreshortening detection system to enable/disable foreshortening detection of stage S124. For example, foreshortening detection is important for therapeutic devices, but may not be for a regular navigation within an anatomical region). Additionally or alternatively, foreshortening manager 102 may automatically enable/disable foreshortening of stage S124 based on the particular type of interventional device 40.

Similarly, foreshortening manager 102 may limit foreshortening alerts critical sections of interventional device 40 so as to reduce alert fatigue. For example, foreshortening indicators apply only to the distal portion of a catheter, or along therapeutic elements of the catheter (e.g., a balloon, a stent, an endograft, etc.). Foreshortening manager 102 may facilitate a tagging by an operator of the foreshortening detection system of regions of interventional device 40 for foreshortening warnings, or adjust automatically tagged regions whereby foreshortening indications may continue to be shown along the entirety of the device, and emphasized at critical sections.

Alternatively or in conjunction with the above, foreshortening manager 102 shown warnings only in salient anatomical regions such as manually/automatically delineated lesions, vessel branches, or tortuous anatomy. Foreshortening manager 102 may facilitate a tagging by an operator of the foreshortening detection system of regions of anatomy for foreshortening warnings, or automatically tagged regions whereby foreshortening indications may continue to be shown throughout the visible anatomy, and emphasized in critical regions.

Foreshortening manager 102 will continue to manage the foreshortening detection until such time the foreshortening has been corrected.

Figure 14A:
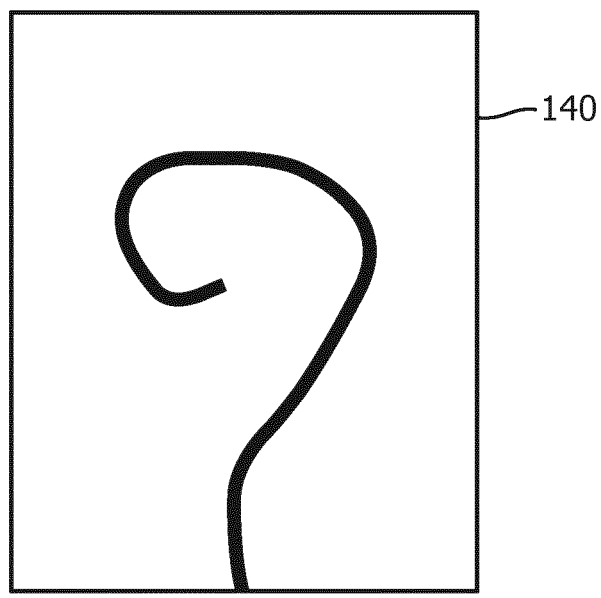
FIGS. 14A-14C illustrate an exemplary foreshortening repositioning recommendation in accordance with the inventive principles of the present disclosure.

To facilitate a further understanding of the inventions of the present disclosure, the following description of FIGS. 14 and 15 teaches exemplary foreshortening detection for various registration procedure involving an interventional tool and an imaging modality. From this description of FIGS. 14 and 15, those having ordinary skill in the art will appreciate how to apply the inventive principles of the present disclosure to practice numerous and various registration procedure involving an interventional tool and an imaging modality.

Shape-to-X-ray Registration. In order to overlay a 3D shape of an interventional device onto a 2D x-ray image, the 3D shape of the interventional device must be registered to the image modality. That registration may be broken down into two primary components.

The first component is a Shape-to-Isocenter (S2Iso): Registers the shape to the isocenter of the c-arm.

The second component is a Perspective Matrix (P): Registers the shape to the perspective of the c-arm (for example, anterior-posterior (AP) or Lateral views).

The transformation between the 3D shape of the interventional device in its original space to the x-ray image space then becomes:

$$\text{Shape}_{x\text{-}ray} = P * S2Iso * \text{Shape}_{orig}$$

Figure 14B:
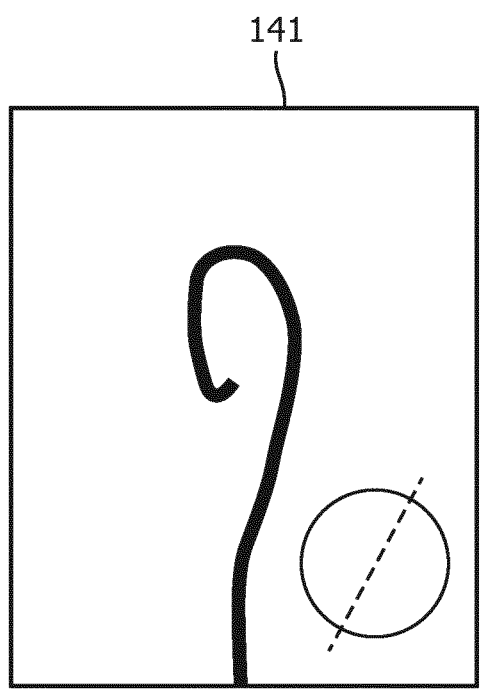
Figure 14C:
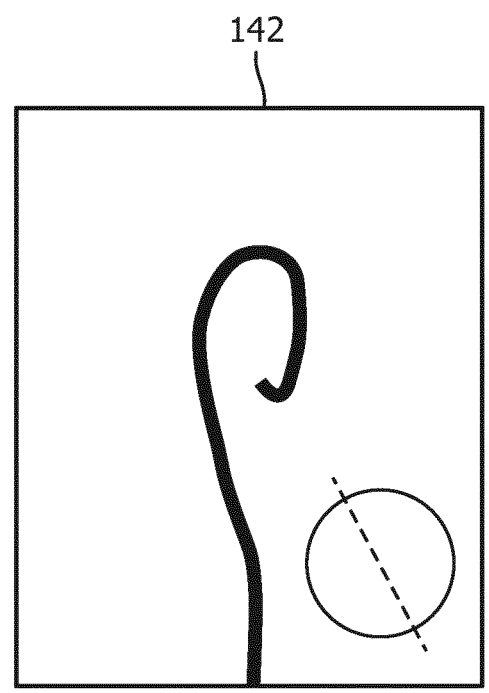
Figure 15A:
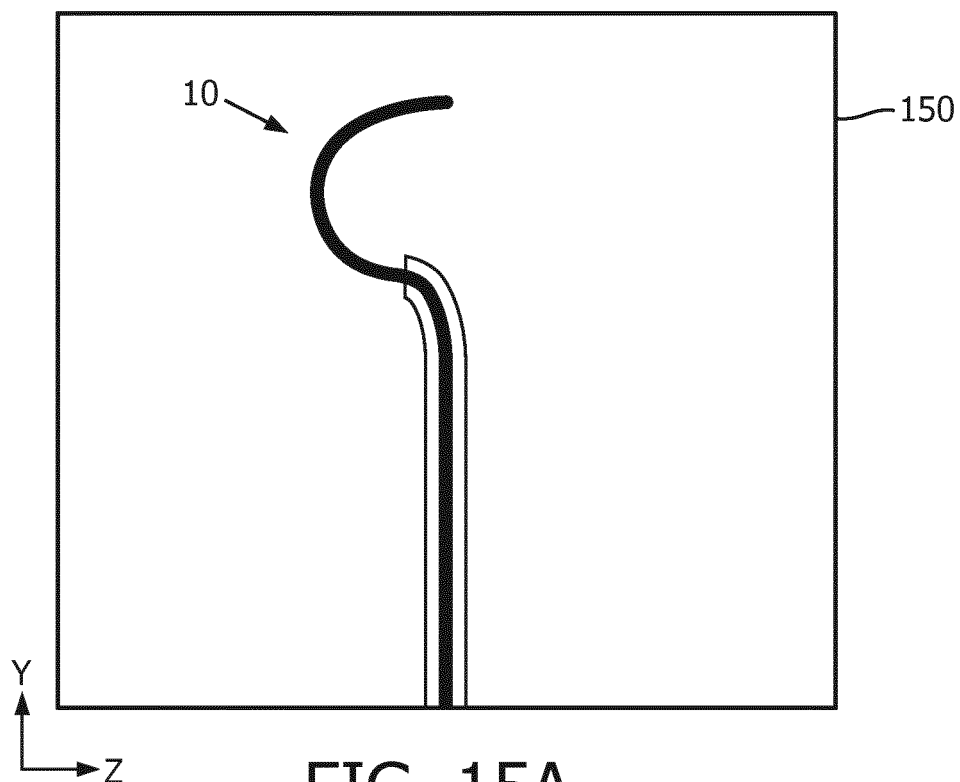
FIGS. 15A and 15B illustrate exemplary registration error and registration accuracy in accordance with the inventive principles of the present disclosure.

A registration workflow as known in the art of the present disclosure requires two X-ray images at projections at least 30 degrees apart in the C-arm gantry angle. For example, X-ray images 141 and 142 shown respectively in FIGS. 14B and 14C are at least 30 degrees apart in the C-arm gantry angle. This requirement reduces the likelihood of inaccurate registration due to foreshortening, but may not eliminate such errors in some cases, such as symmetric perspectives, or projections in which the device crosses with itself.

In practice, candidates for foreshortening include segments of the interventional device that lie in a plane, because in certain C-arm gantry poses these planes may appear as a line, in which points closer to the X-ray source obscure adjacent points along the same planar segment. In accordance with the inventive principles of the present disclosure as previously described herein, during registration such candidates may be predicted by the OSS data and clustering segments that lie in a plane. To reduce the candidate pool to a subset at highest risk for foreshortening, elimination criteria may be applied.

In one embodiment, an elimination criteria may be a minimum segment length that would materially influence registration accuracy.

In a second embodiment, an elimination criteria may be a minimum distal segment position to thereby focus only on "active" parts of the device In a third embodiment, an elimination criteria may be directed to a physically relevant geometry of the interventional device (e.g., a primary longitudinal axis of a guidewire), and this information may be utilized to predict gantry poses at risk for foreshortening In a fourth embodiment, an elimination criteria may be directed to prioritizing salient parts of the interventional device (e.g. therapeutic and steering elements).

In accordance with the inventive principles of the present disclosure as previously described herein, candidate segments of an interventional device that are susceptible to foreshortening are then selectively highlighted during registration. Based on this information, the operator of the foreshortening detection system may select gantry angles to avoid foreshortening, or the foreshortening detection system may suggest such angles. Once registration images are taken, the foreshortening detection system may identify actual occurrences of foreshortening by relating the database of foreshortening candidates to the interventional device as segmented from the images. The foreshortening detection system of the present disclosure may suggest preferred gantry angles, or alternatively estimate the registration error due to foreshortening to allow the operator to decide whether to acquire different poses or reposition the device.

Universal Catheter Registration. Registration for the universal catheter occurs in two situations. The first situation is a registration of device length (e.g., catheters, sheaths, therapy devices, etc.). The second situation is a registration of an important region (e.g., start/stop or other markers for therapy devices, e.g. stent, balloon, valve, IVUS transducer).

One way to perform this registration is to have the operator click on the desired point in the x-ray image. For example, in registration for the length of a catheter, the operator will click on the end of the catheter. The nearest point on the guidewire shape is then selected and the length from the universal catheter hub to that point on the guidewire shape is known. Similarly, to identify the start and end of a stent, the operator can click on each point in the x-ray image and the nearest node on the shape is selected.

Ideally, this registration step would be done from a single x-ray image. This speeds up registration and reduces unnecessary radiation exposure to the patient and physician. However, in order to do this point-based registration from a single shot, the region of interest should not have any foreshortening.

Figure 15B:
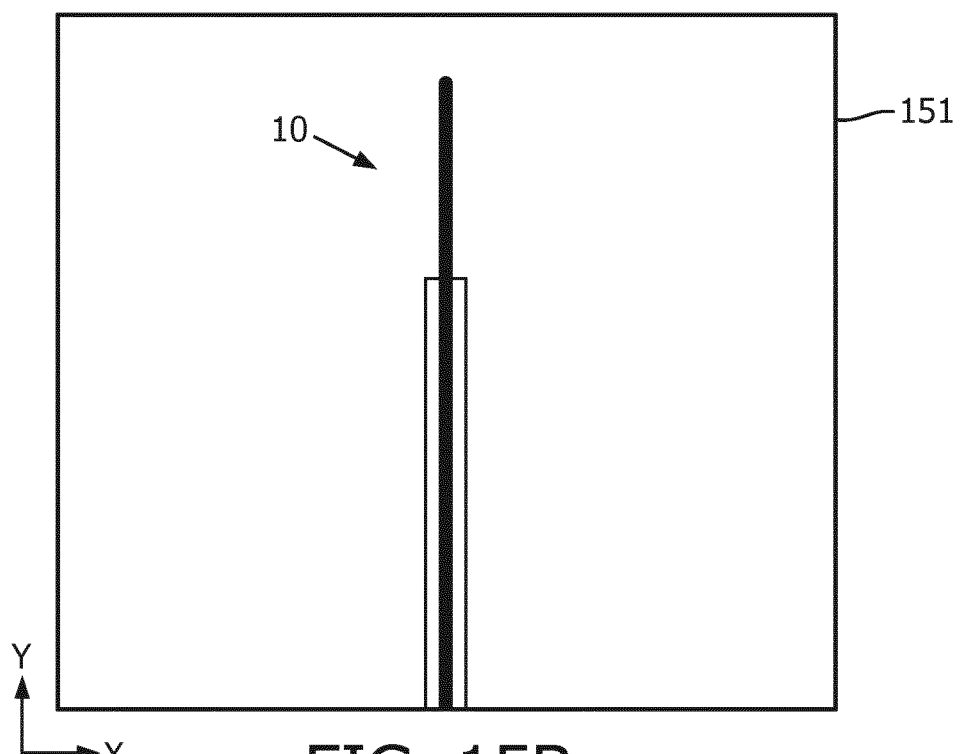

If foreshortening is present, for example as shown in an AP view of FIG. 15B, when the operator clicks on the point in the x-ray image 150, that point will correspond to multiple possible shape-points. Only by seeing the shape in the lateral view of FIG. 15A can the correct point be selected. Extreme foreshortening in the region of registration could lead to inaccuracy in the registration.

The solution, is to flag to the operator when this is occurring. By seeing the foreshortened parts of the shape (via color coding, for example) they can know that this an issue and chose a different image (and c-arm position) for registration. The foreshortening detection system of the present disclosure can suggest a better c-arm position to help with this step. Alternatively, foreshortening detection system of the present disclosure can accept this situation, but factor in the foreshortening to give the operator a predicted registration accuracy or error (+/−2 mm for example).

Referring to FIGS. 1-15, those having ordinary skill in the art will appreciate numerous benefits of the present disclosure including, but not limited to, an improvement over foreshortening monitoring systems, controllers and methods by the inventions of the present disclosure providing for detecting when and where foreshortening is occurring along the length of a shape-sensed device, and for managing an appropriate response to the detected foreshortening (e.g., reporting the foreshortening or recommending a repositioning of an imaging modality to alleviate the foreshortening).

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the inventive principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive OSS foreshortening detection systems, controllers and methods, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An optical shape sensing (OSS) foreshortening detection system, comprising:
    an interventional device comprising an integration of an OSS sensor and at least one interventional tool,
        wherein the OSS sensor is structurally configured to generate shape sensing data informative of a shape of the OSS sensor;
    an OSS foreshortening detection device comprising:
        an OSS shape controller structurally configured to control a reconstruction of a shape of at least a portion of the interventional device derived from a generation of the shape sensing data by the OSS sensor, and
        an OSS foreshortening controller structurally configured to control a monitoring of any foreshortening of the interventional device within an image of the interventional device, wherein the OSS foreshortening controller is further structurally configured to detect a location of an occurrence of a foreshortening of the interventional device within the image of interventional device derived from the reconstruction of the shape of the at least a portion of the interventional device by the OSS shape controller; and
    a structural configuration of the OSS foreshortening controller configured to detect the location of the occurrence of the foreshortening of the interventional device within the image of interventional device, the structural configuration of the OSS foreshortening controller being structurally configured to: identify an image binning of a plurality of shape nodes of the reconstructed shape of the portion of the interventional device indicative of the foreshortening of the interventional device within the image of interventional device; and/or identify a shape variance of the reconstructed shape of the at least a portion of the interventional device indicative of the foreshortening of the interventional device within the image of interventional device; and/or identify at least one vector between adjacent shape nodes of the reconstructed shape of the at least a portion of the interventional device indicative of the foreshortening of the interventional device within the image of interventional device; and/or identify a segment of the reconstructed shape of the at least a portion of the interventional device having an alpha and a curvature indicative of the foreshortening of the interventional device within the image of interventional device; and/or identify a neighborhood density of at least one shape nodes of the reconstructed shape of the portion of the interventional device indicative of the foreshortening of the interventional device within the image of interventional device.

2. The OSS foreshortening detection system of claim 1, wherein the at least a portion of the interventional device includes one of:
    an entire shape of the interventional device;
    a segment of the intervention device between a proximal device node and a distal device node;
    a segment of the interventional device within an anatomical region;
    a segment of the interventional device visible in the image of the interventional device; and
    a segment of the interventional device supporting a therapy device.

3. The OSS foreshortening detection system of claim 1, wherein the image of the interventional device illustrates a navigation of the interventional device within an anatomical region;
    wherein the OSS sensor is operable to generate the shape sensing data informative of the shape of the OSS sensor as the interventional device is navigated within the anatomical region; and
    wherein the OSS foreshortening controller is operable to detect the location of the occurrence of the foreshortening of the interventional device within the image of the interventional device as the interventional device is navigated within the anatomical region.

4. The OSS foreshortening detection system of claim 3, wherein the OSS foreshortening controller is further structurally configured to manage a detection of the location of the occurrence of the foreshortening of the interventional device within the image of the interventional device comprising at least one of:
    the OSS foreshortening controller being structurally configured to manage a display of a foreshortening encoding of the interventional device indicative of the detection of the location of the occurrence of the foreshortening of the interventional device within the image of the interventional device;
    the OSS foreshortening controller being structurally configured to manage a display of an overlay of a foreshortening indicator indicative of the detection of the location of the occurrence of the foreshortening of the interventional device within the image of the interventional device; and
    the OSS foreshortening controller being structurally configured to manage at least one of a textual reporting and an audible reporting of the detection of the location of the occurrence of the foreshortening of the interventional device within the image of the interventional device.

5. The OSS foreshortening detection system of claim 1, wherein the OSS foreshortening controller is operable to detect the location of the occurrence of the foreshortening of the interventional device within the image of the interventional device during a registration of the interventional device and an imaging modality generating imaging data informative of the image of the interventional device.

6. The OSS foreshortening detection system of claim 5, wherein the OSS foreshortening controller is further structurally configured to manage a detection of the location of the occurrence of the foreshortening of the interventional device within the image of interventional device comprising at least one of:
    the OSS foreshortening controller being structurally configured to manage a display of a foreshortening encoding of the interventional device indicative of the detection of the location of the occurrence of the foreshortening of the interventional device within the image of the interventional device;
    the OSS foreshortening controller being structurally configured to manage a display of an overlay of a foreshortening indicator indicative of the detection of the location of the occurrence of the foreshortening of the interventional device within the image of the interventional device; and the OSS foreshortening controller being structurally configured to ascertain at least one repositioning of the imaging modality relative to the interventional device to alleviate the occurrence of the foreshortening of the interventional device within the image of interventional device;

the OSS foreshortening controller being structurally configured to estimate at least one of a registration error and a registration accuracy based on the detection of the location of the occurrence of the foreshortening of the interventional device within the image of interventional device;

the OSS foreshortening controller being structurally configured to manage at least one of a textual reporting and an audible reporting at least one of an ascertained repositioning of the imaging modality relative to the interventional device and an estimation of the at least one of the registration error and the registration accuracy; and the OSS foreshortening controller being structurally configured to manage a recommendation of a viewing angle of an imaging modality for at least one of a segmentation and a registration of the image of the interventional device.

7. The OSS foreshortening detection system of claim 1, wherein the interventional tool is one of a vascular interventional tool, an endoluminal interventional tool and an orthopedic interventional tool.

8. An OSS foreshortening detection device for an interventional device comprising an integration of an OSS sensor and at least one interventional tool, the OSS sensor for generating shape sensing data informative of a shape of the OSS sensor, the OSS foreshortening detection device comprising:

an OSS shape controller structurally configured to control a reconstruction of a shape of at least a portion of the interventional device derived from a generation of the shape sensing data by the OSS sensor; and an OSS foreshortening controller structurally configured to control a monitoring of any foreshortening of the interventional device within an image of the interventional device, wherein the OSS foreshortening controller is further structurally configured to detect a location of an occurrence of a foreshortening of the interventional device within the image of interventional device derived from the reconstruction of at least the portion of the shape of the interventional device by the OSS shape controller; and a structural configuration of the OSS foreshortening controller to detect the location of the occurrence of the foreshortening of the interventional device within the image of interventional device, the structural configuration of the OSS foreshortening controller being structurally configured to: identify an image binning of a plurality of shape nodes of the reconstructed shape of the portion of the interventional device indicative of the foreshortening of the interventional device within the image of interventional device; and/or identify a shape variance of the reconstructed shape of the at least a portion of the interventional device indicative of the foreshortening of the interventional device within the image of interventional device; and/or identify at least one vector between adjacent shape nodes of the reconstructed shape of the at least a portion of the interventional device indicative of the foreshortening of the interventional device within the image of interventional device; and/or identify a segment of the reconstructed shape of the at least a portion of the interventional device having an alpha and a curvature indicative of the foreshortening of the interventional device within the image of interventional device; and/or identify a neighborhood density of at least one shape nodes of the reconstructed shape of the portion of the interventional device indicative of the foreshortening of the interventional device within the image of interventional device.

9. The OSS foreshortening detection device claim 8, wherein the at least a portion of the interventional device includes one of:
an entire shape of the interventional device;
a segment of the intervention device between a proximal device node and a distal device node;
a segment of the interventional device within an anatomical region;
a segment of the interventional device visible in the image of the interventional device; and
a segment of the interventional device supporting a therapy device.

10. The OSS foreshortening detection device claim 8, wherein the image of the interventional device illustrates a navigation of the interventional device within an anatomical region;
wherein the OSS sensor is operable to generate the shape sensing data informative of the shape of the OSS sensor as the interventional device is navigated within the anatomical region; and
wherein the OSS foreshortening controller is operable to detect the location of the occurrence of the foreshortening of the interventional device within the image of the interventional device as the interventional device is navigated within the anatomical region.

11. The OSS foreshortening detection device claim 10, wherein the OSS foreshortening controller is further structurally configured to manage a detection of the location of the occurrence of the foreshortening of the interventional device within the image of the interventional device comprising at least one of:
the OSS foreshortening controller being structurally configured to manage a display of a foreshortening encoding of the interventional device indicative of the detection of the location of the occurrence of the foreshortening of the interventional device within the image of the interventional device;
the OSS foreshortening controller being structurally configured to manage a display of an overlay of a foreshortening indicator indicative of the detection of the location of the occurrence of the foreshortening of the interventional device within the image of the interventional device; and
the OSS foreshortening controller being structurally configured to manage at least one of a textual reporting and an audible reporting of the detection of the location of the occurrence of the foreshortening of the interventional device within the image of the interventional device.

12. The OSS foreshortening detection device claim 8, wherein the OSS foreshortening controller is operable to detect the location of the occurrence of the foreshortening of the interventional device within the image of the interventional device during a registration of the interventional device and an imaging modality generating imaging data informative of the image of the interventional device.

13. The OSS foreshortening detection device claim 12, wherein the OSS foreshortening controller is further structurally configured to manage a detection of the location of the occurrence of the foreshortening of the interventional device within the image of interventional device comprising at least one of:
- the OSS foreshortening controller being structurally configured to manage a display of a foreshortening encoding of the interventional device indicative of the detection of the location of the occurrence of the foreshortening of the interventional device within the image of the interventional device;
- the OSS foreshortening controller being structurally configured to manage a display of an overlay of a foreshortening indicator indicative of the detection of the location of the occurrence of the foreshortening of the interventional device within the image of the interventional device; and
- the OSS foreshortening controller being structurally configured to ascertain at least one repositioning of the imaging modality relative to the interventional device to alleviate the occurrence of the foreshortening of the interventional device within the image of interventional device;
- the OSS foreshortening controller being structurally configured to estimate at least one of a registration error and a registration accuracy based on the detection of the location of the occurrence of the foreshortening of the interventional device within the image of interventional device; and
- the OSS foreshortening controller being structurally configured to manage at least one of a textual reporting and an audible reporting at least one of an ascertained repositioning of the imaging modality relative to the interventional device and an estimation of the at least one of the registration error and the registration accuracy; and
- the OSS foreshortening controller being structurally configured to manage a recommendation of a viewing angle of an imaging modality for at least one of a segmentation and a registration of the image of the interventional device.

14. An OSS foreshortening detection method for an interventional device comprising an integration of an OSS sensor and at least one interventional tool, the OSS sensor for generating shape sensing data informative of a shape of the OSS sensor, the OSS foreshortening detection method comprising:
- generating with the OSS sensor shape sensing data informative of a shape of the OSS sensor;
    - controlling with an OSS foreshortening detection device: a reconstruction of a shape of at least a portion of the interventional device derived from a generation of the shape sensing data by OSS sensor; and a monitoring of any foreshortening of the interventional device within an image of the interventional device comprising the OSS foreshortening controller detecting a location of any occurrence of a foreshortening of the interventional device within the image of interventional device derived from the reconstruction of the shape of the at least a portion of the interventional device by the OSS shape controller;
- detecting, with the OSS foreshortening detection device, a location of any occurrence of the foreshortening of the interventional device within the image of interventional device derived from the reconstruction of the shape of the interventional device by the OSS shape controller, wherein the OSS foreshortening controller executes at least one of:
    - an identification of an image binning of a plurality of shape nodes of the reconstructed shape of the portion of the interventional device indicative of the foreshortening of the interventional device within the image of interventional device;
    - an identification of a shape variance of the reconstructed shape of the at least a portion of the interventional device indicative of the foreshortening of the interventional device within the image of interventional device;
    - an identification of at least one vector between adjacent shape nodes of the reconstructed shape of the at least a portion of the interventional device indicative of the foreshortening of the interventional device within the image of interventional device;
    - an identification of a segment of the reconstructed shape of the at least a portion of the interventional device having an alpha and a curvature indicative of the foreshortening of the interventional device within the image of interventional device; and
    - an identification of a neighborhood density of at least one shape nodes of the reconstructed shape of the portion of the interventional device indicative of the foreshortening of the interventional device within the image of interventional device.

15. The OSS foreshortening detection method of claim 14, wherein the at least a portion of the interventional device includes one of:
- an entire shape of the interventional device;
- a segment of the intervention device between a proximal device node and a distal device node;
- a segment of the interventional device within an anatomical region;
- a segment of the interventional device visible in the image of the interventional device; and
- a segment of the interventional device supporting a therapy device.

16. The OSS foreshortening detection method of claim 14,
- wherein the OSS sensor is generating the shape sensing data informative of a shape of the OSS sensor as the interventional device is navigated within an anatomical region; and
- wherein the OSS foreshortening device is detecting a location of any occurrence of the foreshortening of the interventional device within the image of interventional device within the anatomical region derived from the reconstruction of the shape of the interventional device by the OSS shape controller.

17. The OSS foreshortening detection method of claim 14,
- wherein the OSS foreshortening device is detecting a location of any occurrence of the foreshortening of the interventional device within the image of interventional device during a registration of the interventional device and an imaging modality generating imaging data informative of the image of the interventional device.

* * * * *